United States Patent
Rocco et al.

(10) Patent No.: US 12,127,932 B2
(45) Date of Patent: Oct. 29, 2024

(54) COMPOSITE SCAFFOLD FOR THE REPAIR, RECONSTRUCTION, AND REGENERATION OF SOFT TISSUES

(71) Applicant: CONMED Corporation, Largo, FL (US)

(72) Inventors: Kevin A. Rocco, New Haven, CT (US); Bhavana Mohanraj, Philadelphia, PA (US); Jeffrey Ott, New Haven, CT (US); Justin Bendigo, Reading, PA (US); Jacob Edward Komenda, New Haven, CT (US); Mark Theodore Aronson, Midlothian, VA (US); Andrew James Carter, Stow, MA (US)

(73) Assignee: CONMED Corporation, Largo, FL (US)

( * ) Notice: Subject to any disclaimer, the term of this patent is extended or adjusted under 35 U.S.C. 154(b) by 0 days.

(21) Appl. No.: 18/132,600

(22) Filed: Apr. 10, 2023

(65) Prior Publication Data
US 2023/0390047 A1   Dec. 7, 2023

Related U.S. Application Data

(63) Continuation of application No. 17/694,012, filed on Mar. 14, 2022, now Pat. No. 11,622,847, which is a
(Continued)

(51) Int. Cl.
*A61F 2/08* (2006.01)
*A61F 2/00* (2006.01)
(Continued)

(52) U.S. Cl.
CPC ............. *A61F 2/08* (2013.01); *A61F 2/0063* (2013.01); *A61L 27/14* (2013.01); *A61L 27/18* (2013.01);
(Continued)

(58) Field of Classification Search
CPC .. A61F 2/08; A61F 2/0063; A61F 2002/0068; A61F 2002/0081;
(Continued)

(56) References Cited

U.S. PATENT DOCUMENTS

| 5,209,849 A | 5/1993 | Hu et al. |
| 5,380,328 A | 1/1995 | Morgan |

(Continued)

FOREIGN PATENT DOCUMENTS

| JP | 2007098118 A | 4/2007 |
| WO | 0062829 A1 | 10/2000 |
| WO | 2017210251 A1 | 12/2017 |

OTHER PUBLICATIONS

Gokarneshan, N., et al. Weaving of 3D fabrics: A critical appreciation of the devlopments. Textile Progress. vol. 41, No. 1, 2009, pp. 1-58.
(Continued)

*Primary Examiner* — Yashita Sharma
(74) *Attorney, Agent, or Firm* — ArentFox Schiff LLP; Bruce D. Jobse

(57) ABSTRACT

A composite scaffold having a highly porous interior with increased surface area and void volume is surrounded by a flexible support structure that substantially maintains its three-dimensional shape under tension and provides mechanical reinforcement during repair or reconstruction of soft tissue while simultaneously facilitating regeneration of functional tissue.

31 Claims, 31 Drawing Sheets

Related U.S. Application Data continuation of application No. 17/372,999, filed on Jul. 12, 2021, now Pat. No. 11,273,026, which is a continuation of application No. 16/785,524, filed on Feb. 7, 2020, now Pat. No. 11,058,532.

(60) Provisional application No. 62/970,620, filed on Feb. 5, 2020, provisional application No. 62/802,391, filed on Feb. 7, 2019.

(51) Int. Cl.
```
A61L 27/14      (2006.01)
A61L 27/18      (2006.01)
A61L 27/24      (2006.01)
A61L 27/26      (2006.01)
A61L 27/48      (2006.01)
A61L 27/52      (2006.01)
A61L 27/56      (2006.01)
A61L 27/58      (2006.01)
D06N 3/00       (2006.01)
A61L 27/34      (2006.01)
A61L 27/50      (2006.01)
D04B 21/12      (2006.01)
```

(52) U.S. Cl.
CPC .............. *A61L 27/24* (2013.01); *A61L 27/26* (2013.01); *A61L 27/48* (2013.01); *A61L 27/52* (2013.01); *A61L 27/56* (2013.01); *A61L 27/58* (2013.01); *D06N 3/0043* (2013.01); *A61F 2002/0068* (2013.01); *A61F 2002/0081* (2013.01); *A61F 2210/0004* (2013.01); *A61F 2210/0057* (2013.01); *A61F 2210/0061* (2013.01); *A61F 2210/0076* (2013.01); *A61F 2240/001* (2013.01); *A61L 27/34* (2013.01); *A61L 27/50* (2013.01); *A61L 2430/10* (2013.01); *D04B 21/12* (2013.01); *D10B 2509/08* (2013.01); *Y10T 428/249921* (2015.04); *Y10T 428/249978* (2015.04); *Y10T 442/2484* (2015.04); *Y10T 442/419* (2015.04)

(58) Field of Classification Search
CPC ...... A61F 2210/0004; A61F 2210/0057; A61F 2210/0061; A61F 2210/0076; A61F 2240/001; A61F 2/0077; A61F 2240/004; A61L 27/14; A61L 27/18; A61L 27/24; A61L 27/26; A61L 27/48; A61L 27/52; A61L 27/56; A61L 27/58; A61L 27/34; A61L 27/50; A61L 2430/10; A61L 2430/34; D06N 3/0043; D04B 21/12; D04B 21/16; D10B 2509/08; D10B 2403/021; Y10T 428/249921; Y10T 428/249978; Y10T 442/2484; Y10T 442/419; C08L 71/02; C08L 89/06
See application file for complete search history.

(56) References Cited

U.S. PATENT DOCUMENTS

| | | |
|---|---|---|
| 6,113,624 A | 9/2000 | Bezwada et al. |
| 6,391,333 B1 | 5/2002 | Li et al. |
| 6,471,993 B1 | 10/2002 | Shastri et al. |
| 6,508,897 B1 | 1/2003 | Yamaguchi et al. |
| 6,599,524 B2 | 7/2003 | Li et al. |
| 6,838,493 B2 | 1/2005 | Williams et al. |
| 7,192,437 B2 | 3/2007 | Shalaby |
| 7,208,222 B2 | 4/2007 | Rolfe et al. |
| 7,229,441 B2 | 6/2007 | Trieu et al. |
| 7,323,190 B2 | 1/2008 | Chu et al. |
| 7,416,564 B2 | 8/2008 | Kim et al. |
| 7,807,192 B2 | 10/2010 | Li et al. |
| 8,029,575 B2 | 10/2011 | Borden |
| 8,551,519 B2 | 10/2013 | Bezwada |
| 8,821,917 B2 | 9/2014 | Li et al. |
| 8,834,578 B2 | 9/2014 | Bayon et al. |
| 8,992,411 B2 | 3/2015 | Koullick et al. |
| 9,039,782 B2 | 5/2015 | Atala et al. |
| 9,382,422 B2 | 7/2016 | Owens et al. |
| 10,058,409 B2 | 8/2018 | Palmer et al. |
| 2002/0161450 A1 | 10/2002 | Doi et al. |
| 2003/0044444 A1 | 3/2003 | Malaviya et al. |
| 2003/0072784 A1 | 4/2003 | Williams |
| 2003/0106347 A1 | 6/2003 | Kost |
| 2003/0114936 A1 | 6/2003 | Sherwood et al. |
| 2003/0133967 A1 | 7/2003 | Ruszczak et al. |
| 2004/0088053 A1 | 5/2004 | Serhan et al. |
| 2004/0101518 A1 | 5/2004 | Vacanti et al. |
| 2005/0234336 A1 | 10/2005 | Beckman et al. |
| 2006/0148917 A1 | 7/2006 | Radwanski et al. |
| 2006/0193899 A1 | 8/2006 | Sawhney |
| 2006/0195011 A1 | 8/2006 | Arnal et al. |
| 2007/0041952 A1 | 2/2007 | Guilak et al. |
| 2007/0116737 A1 | 5/2007 | Favis et al. |
| 2007/0142698 A1 | 6/2007 | Bourne et al. |
| 2007/0254005 A1 | 11/2007 | Pathak et al. |
| 2008/0033392 A1 | 2/2008 | Gaserod et al. |
| 2008/0300683 A1 | 12/2008 | Altman et al. |
| 2009/0022771 A1 | 1/2009 | Lynn et al. |
| 2009/0074832 A1 | 3/2009 | Zussman et al. |
| 2009/0163612 A1 | 6/2009 | Brady et al. |
| 2010/0217169 A1 | 8/2010 | Ingimundarson et al. |
| 2010/0279905 A1 | 11/2010 | Glen, Jr. et al. |
| 2011/0264237 A1 | 10/2011 | Bayon et al. |
| 2012/0095482 A1 | 4/2012 | Peterson et al. |
| 2012/0128739 A1 | 5/2012 | Nygaard et al. |
| 2012/0214222 A1 | 8/2012 | Sannino et al. |
| 2013/0131825 A1 | 5/2013 | Ganey |
| 2013/0209779 A1 | 8/2013 | Iida et al. |
| 2013/0282140 A1 | 10/2013 | Ringeisen et al. |
| 2013/0345728 A1 | 12/2013 | Lecuivre |
| 2014/0081296 A1 | 3/2014 | Palmer et al. |
| 2014/0194989 A1 | 7/2014 | Bonutti |
| 2015/0039097 A1 | 2/2015 | Biris |
| 2015/0056131 A1 | 2/2015 | Bernasconi et al. |
| 2015/0148823 A1 | 5/2015 | Mortarino et al. |
| 2015/0238318 A1 | 8/2015 | McCullen |
| 2016/0081824 A1 | 3/2016 | Harrington et al. |
| 2016/0213456 A1 | 7/2016 | Mortarino |
| 2017/0014552 A1 | 1/2017 | Martin et al. |
| 2017/0035542 A1 | 2/2017 | Koullick et al. |
| 2017/0095351 A1 | 4/2017 | Liu |
| 2017/0143872 A1 | 5/2017 | Limem et al. |
| 2017/0209251 A1 | 7/2017 | Francois et al. |
| 2017/0273775 A1 | 9/2017 | Rocco et al. |
| 2018/0028232 A1 | 2/2018 | Fonte et al. |
| 2018/0028317 A1 | 2/2018 | Schlachter |
| 2018/0116837 A1 | 5/2018 | Ramzipoor et al. |
| 2018/0168797 A1 | 6/2018 | Koob et al. |
| 2018/0214603 A1 | 8/2018 | Huang et al. |
| 2019/0117375 A1 | 4/2019 | Snedeker |

OTHER PUBLICATIONS

Chen, Guoping, et al. The use of a novel PLGA fiber/collagen composite web as a scaffold for engineering of articular cartilage tissue with adjustable thickness. Wiley Periodicals, Inc. 2003, pp. 1170-1180.

Evaldas Baličiūnas et al., "Combination of thermal extrusion printing and ultrafast laser fabrication for the manufacturing of 3D composite scaffolds," Proc. SPIE 8972, Frontiers in Ultrafast Optics: Biomedical, Scientific, and Industrial Applications XIV, 89721N (Mar. 7, 2014); (Year: 2014).

COMPOSITE SCAFFOLD FOR THE REPAIR, RECONSTRUCTION, AND REGENERATION OF SOFT TISSUES

CROSS REFERENCE TO RELATED APPLICATIONS

This application claims the benefit of U.S. Provisional Application No. 62/802,391, filed Feb. 7, 2019 and U.S. Provisional Application No. 62/970,620, filed Feb. 5, 2020, the entire contents of which are incorporated herein by this reference for all purposes.

Further, the entire contents of the following applications, filed by the same applicant on an even date herewith, are incorporated herein by this reference for all purposes:

U.S. patent application Ser. No. 16/785,590, filed on Feb. 7, 2020, entitled "COMPOSITE SCAFFOLD FOR THE REPAIR, RECONSTRUCTION, AND REGENERATION OF SOFT TISSUES,";

U.S. patent application Ser. No. 16/785,512, filed on Feb. 7, 2020, entitled "COMPOSITE SCAFFOLD FOR THE REPAIR, RECONSTRUCTION, AND REGENERATION OF SOFT TISSUES,";

U.S. patent application Ser. No. 16/785,518, filed on Feb. 7, 2020, entitled "COMPOSITE SCAFFOLD FOR THE REPAIR, RECONSTRUCTION, AND REGENERATION OF SOFT TISSUES,"; and U.S. patent application Ser. No. 16/785,529, filed on Feb. 7, 2020, entitled "COMPOSITE SCAFFOLD FOR THE REPAIR, RECONSTRUCTION, AND REGENERATION OF SOFT TISSUES,".

FIELD OF THE INVENTION

The disclosure relates to soft tissue repair and reconstruction, and, more specifically, to a composite scaffold useful for stabilizing soft tissue injuries or defects while facilitating the regeneration of new tissue.

BACKGROUND OF THE INVENTION

Biologic and synthetic scaffolds for use in tissue engineering applications and surgical repairs and reconstructions are known, however, few are capable of providing the optimal combination of a sufficient: porosity for cellular ingrowth, biologic matrix and surface area for cell migration and proliferation, interconnected void volume and dimensions for meaningful extracellular matrix deposition and tissue regeneration, composite mechanical properties and mechanical load sharing with local tissues to encourage functional tissue maturation while resisting collapse or compression under said mechanical loading, and bio-resorption timeline which supports the tissue repair through complete healing while facilitating the regeneration of functional tissue.

Some scaffolds, such as hernia mesh have sufficient mechanical properties to complete a surgical repair, but lack the behavioral characteristics which are not optimally suited for healing and regeneration of soft tissues of the knee, ankle, shoulder elbow and hand, and non-musculoskeletal soft tissue. Many such scaffolds are made of permanent synthetic polymers which can elicit acute or chronic adverse inflammation, pain, or complications. In addition, many mesh-like scaffolds are essentially two-dimensional with insufficient surface area for cell ingrowth and insufficient void volume for bulk tissue regeneration, and, therefore are not conducive to regenerating functional tissue. Conversely, most biologic scaffolds for the repair and reconstruction of soft tissues are derived from bulk tissues harvested and processed from either allogenous or xenogeneous sources, and often have slow or incomplete healing due to any combination of bulk architecture, tissue source, and processing method. Highly processed biologic materials that are reconstructed into entirely new architectures, such as collagen gels or sponges, can be produced with suitable porosity for tissue ingrowth but lacking suitable strength and resistance to collapse for use for ligament or tendon repair.

Many of the commercially available scaffolds composed of fibers have appropriate mechanical properties but are inadequate for functional tissue regeneration due to shortcomings of the architecture derived from existing manufacturing processes such as knitting, weaving, braiding, and non-woven methods such electrospinning, pneumatic-spinning, melt-blowing etc.; this is because the fibers have insufficient space between filaments and/or fiber bundles (inadequate porosity or void volume or density—e.g. typical of electrospun textiles), or too little surface area, void volume and dimensions for meaningful tissue regeneration (e.g. typical planar warp knit textiles or braids, or fiber bundles), or when adequate void volumes are created, it is either not contiguous on a cellular and biologically-relevant scale, or it collapses as the structure is tensioned.

Accordingly, a need exists for a scaffold and method of repairing or regenerating ligament tissue.

Another need exists for a scaffold which is composite, i.e. mimics the mechanical properties of native tendons and ligaments.

A further need exists for a scaffold which provides adequate porosity and interconnected void volume for cellular infiltration and tissue ingrowth, while substantially maintaining its shape under loading or tension.

A still further need exists for a scaffold which is bioabsorbable over a period of time which supports healing for a number of weeks or months while facilitating the regeneration of functional tissue capable of bearing mechanical load following scaffold resorption.

Another need exists for a scaffold which minimizes synthetic polymer density and maximizes the surface area to volume ratio of the scaffold, thereby limiting the foreign body response and improving tissue regeneration.

Yet another need exists for a scaffold which has an adjustable length, width, and height for different procedures.

Another need exists for which a bioresorbable scaffold regenerates tissue of sufficient strength and thickness following complete resorption of scaffold material.

Yet another need exists for a scaffold which provides a secondary support matrix capable of encouraging cell growth spaced apart from the scaffold to encourage tendon or ligament tissue ingrowth.

Still another need exists for this scaffold to have engineered regions of variable dimensions, density, porosity, material composition, fiber type, and surface characteristics to improve the tissue regeneration and or surgical handling and implantation.

SUMMARY OF THE INVENTION

Disclosed is a composite scaffold for ligament or tendon repair that provides mechanical reinforcement for the repaired and healing tendon or ligament. In embodiments, the composite scaffold comprises a support structure which defines a void volume. A porous material or hydrogel is disposed within a void volume of the support structure. The support structure reinforces and supports the porous material/hydrogel, enhance the tensile strength of the scaffold and resists compression as the scaffold is extended or subject to elongation forces. The porous material/hydrogel has a porosity and void volume that allows adequate extracellular matrix deposition and new functional tissue regeneration. In embodiments, the void volume is contiguous or essentially contiguous along the long axis of the scaffold, which allows cells to fully migrate within the device and for new tissue to form with an orientation in the axial direction of the scaffold, while being protected from significant collapse, compression or excessive dilation during mechanical loading or tensioning of the scaffold. Optionally, all or part of the scaffold may be hydrated with biologic fluids such as blood, bone marrow aspirate, platelet rich plasma, autologous or allogeneic cells to modulate or direct the immune response and further facilitate and accelerate healing and tissue regeneration.

The disclosed composite scaffold possesses a large surface area for cellular proliferation and migration, but also a sufficiently large, interconnected void space to allow tissue ingrowth, extracellular matrix deposition, and biomechanical remodeling into functional tissue. Further, the scaffold possesses the ability to maintain a highly porous structure under tension, e.g. resisting collapse, during a surgical procedure and following implantation thereby maintaining the ability for cell infiltration and new tissue ingrowth throughout the entire scaffold under physiological loadings. These loadings are mechanically shared between the device and local tissue due to the composite mechanical properties of the device, i.e., prevents stress shielding of proximal, repaired, or native tissues, as well as the developing neotissue within the scaffold itself. Further, these composite mechanical properties encourage the mechanobiological signaling of cells within the scaffold to differentiate and form load-bearing, oriented extracellular matrix and connective tissues. The disclosed composite scaffold can be manufactured using various different textile and composite manufacturing methods, and is not limited to a singular manufacturing technology.

The disclosed composite scaffold provides a highly porous and flexible structure that substantially maintains its three-dimensional shape under tension and provides mechanical reinforcement of the repair or reconstruction-first via scaffold mechanical properties, and subsequently, through newly regenerated functional tissue as the scaffold is resorbed.

The disclosed scaffold may have distinct regions with different mechanical properties to facilitate fixation or differential tissue regeneration. In embodiments, the composite scaffold may be impregnated with cells, biologic aspirates or bio-active agents prior to implantation to create a biological "band-aid". In other embodiments, the bio-inductive scaffold is seeded with auto-, allo-, or xeno-genous derived cells for a temporary pre-culture period to allow the cells to elaborate a collagen-rich extracellular matrix within the scaffold. The scaffold may then be processed and/or decellularized to leave a fiber-reinforced tissue scaffold that can be subsequently implanted, or may be implanted "as is". The disclosed scaffold may be compatible with a variety of currently available fixation methods, e.g. suture, suture anchors, tacks, staples, etc.

The disclosed composite scaffold provides a mechanism to space tissue fibers apart from each other within the scaffold to provide room for ingrowth for higher quality tissue not disrupted by polymer or the corresponding inflammation. The microporous matrix acts as a stabilizer that helps to maintain such space and allows for a larger surface for cells to grow so tissue can mature while the primary fiber of the scaffold still retains strength. If the microporous matrix resorbs at a faster rate than the support structure, a complete mass loss of the microporous matrix can occur so that tissue can reclaim and remodel within the newly created volume in vivo, while the primary support structure retains strength, allowing cells to first invade and encapsulate the structure but also create functional tissue over time. Additionally, if a natural material is used to create the secondary matrix, such as collagen, a reduction in scaffold inflammation may result and further encourage cell ingrowth into the scaffold while not in contact with any of the synthetic fibers comprising the support structure.

According to one aspect of the disclosure, a composite scaffold comprises a first matrix and an optional second matrix which may be integrally formed with one another to maximize the surface area to volume ratio of the scaffold while still maintaining mechanical and structural integrity. According to embodiments, the first matrix may be implemented with the three-dimensional textile structure comprising first and a second support layers spaced apart to define an interior space or void therebetween. Multiple spacer elements extend between the first and second support layers to maintain the support layers separate. The first and second support layers may have different geometries, fibers, or material compositions. The first and second support layers and spacer elements may be implemented as a three dimensional textile comprising multi-layer knitted or woven surfaces of multifilament fibers or monofilament fibers, or any combination thereof, formed of any combination of synthetic bioresorbable polymers, natural polymers and/or additives. The second matrix is disposed within the void space between and proximate the first and second support layers of the first support matrix. The second matrix may be implemented with a low-density, high surface area material comprising any of a sponge, foam, felt, textured fibers or yarns, collagen or tissue-derived material, or any combination thereof. The first and second matrices of the composite scaffold may have the same or different structure, composition, and bioabsorbable characteristics to facilitate optimal regeneration of functional tissue.

In one embodiment, the composite scaffold may have a minimum thickness of approximately greater than or equal to 1 mm. The thickness of the scaffold may be uniform along a length thereof or may vary in a repeating or non-repeating manner, depending on the particular application for which the scaffold will be utilized. In other embodiments, the disclosed composite scaffold may have length dimensions between approximately 2 to 1000 mm, depending on the particular application for which the scaffold will be utilized. The disclosed scaffolds may be manufactured in different incremental lengths or may be manufactured in lengths which may be cut or customized by practitioner as desired or as appropriate for a specific procedure.

According to one aspect of the disclosure, a composite scaffold comprises: a microporous matrix having a multitude of interconnected pores opening to an exterior surface of the microporous matrix and collectively defining void space; and a structure supporting the microporous matrix; wherein a surface area of the composite scaffold is between approximately 0.6 m$^2$/gram and 1.2 m$^2$/gram.

According to another aspect of the disclosure, a composite scaffold comprises: a microporous matrix having a multitude of interconnected pores opening to an exterior surface of the microporous matrix and collectively defining void space having a measurable volume; and a structure supporting the microporous matrix; wherein the volume of void space is between approximately 3.5 cm³/gram and 7 cm³/gram.

According to another aspect of the disclosure, a composite scaffold comprises: a microporous matrix having a multitude of interconnected pores opening to an exterior surface of the microporous matrix and collectively defining void space having a measurable volume, and wherein the void space volume is between approximately 80% and 90% of a measurable volume of the biomimetic scaffold.

According to another aspect of the disclosure, a composite scaffold comprises: a microporous matrix having a multitude of interconnected pores opening to an exterior surface of the microporous matrix and collectively defining void space having a measurable volume, and wherein the scaffold has a permeability of between approximately 1400 and 2600 millidarcy.

According to another aspect of the disclosure, a composite scaffold comprises: a microporous matrix having a multitude of interconnected pores opening to an exterior surface of the microporous matrix and collectively defining void space having a measurable volume, wherein the multitude of interconnected pores have a tortuosity of approximately between 5 µm/µm and 45 µm/µm, wherein the tortuosity defines a ratio of actual flow path length to straight distance between first and second ends of the microporous matrix.

According to another aspect of the disclosure, a composite scaffold comprises: a microporous matrix having a multitude of interconnected pores opening to an exterior surface of the microporous matrix and collectively defining void space having a measurable volume, a structure supporting the microporous matrix; and wherein the void space surface area to volume support structure volume is between approximately 7,000 cm²/cm³ and 14,000 cm²/cm³.

According to another aspect of the disclosure, a composite scaffold comprises: a support structure defining an interior space; and a microporous matrix disposed within the interior space of the support structure, wherein the microporous matrix comprises a plurality of interconnected pores having a median pore size of between approximately 12 µm to 50 µm.

According to another aspect of the disclosure, a composite scaffold comprises: a support structure defining an interior space; and a microporous matrix disposed within the interior space of the support structure, the microporous matrix having a multitude of interconnected pores collectively defining void space; wherein at least approximately 60% of the void space comprises pores having a size dimension of 10 µm or greater.

According to another aspect of the disclosure, a composite scaffold comprises: a microporous matrix having a multitude of interconnected pores collectively defining void space opening to an exterior surface of the microporous matrix; and a structure supporting the microporous matrix; the biomimetic scaffold having a measurable dry weight value representing a weight of the biomimetic scaffold in a substantially dry state and a measurable dry volume value representing a volume of the biomimetic scaffold in a substantially dry state, wherein an increase of between approximately 200% and 600% of the weight value of the biomimetic scaffold from fluid absorption changes the dry volume value of the biomimetic scaffold between approximately 0% and 10%.

According to another aspect of the disclosure, a composite scaffold comprises: a microporous matrix having a multitude of interconnected pores collectively defining void space opening to an exterior surface of the microporous matrix; and a structure supporting the microporous matrix; the composite scaffold having a measurable dry weight value representing a weight of the composite scaffold in a substantially dry state and a measurable dry length value representing a dimensional parameter of the composite scaffold in a substantially dry state, wherein an increase of between approximately 200% and 600% of the weight value of the composite scaffold from fluid absorption changes the dry length value of the composite scaffold by less than between approximately 0% and 3%.

According to another aspect of the disclosure, a composite scaffold comprises: a microporous matrix having a multitude of interconnected pores collectively defining void space opening to an exterior surface of the microporous matrix; and a structure supporting the microporous matrix; the composite scaffold having a measurable dry weight value representing a weight of the composite scaffold in a substantially dry state and a measurable cross sectional profile value representing a dimensional parameter of the composite scaffold in a substantially dry state, wherein an increase of between approximately 200% and 600% of the weight value of the composite scaffold from fluid absorption changes the cross sectional profile value of the composite scaffold by between approximately 0% and 10%.

According to another aspect of the disclosure, a composite scaffold comprises: a microporous matrix having a multitude of interconnected pores collectively defining void space opening to an exterior surface of the microporous matrix; and a structure supporting the microporous matrix; wherein a smallest dimension of the composite scaffold is a thickness dimension approximately greater than or equal to 1 mm, and wherein the composite scaffold has a swelling profile measurable by a less than or equal to 10% change in measured wet thickness of the composite scaffold in comparison to a measured dry thickness of the composite scaffold.

According to another aspect of the disclosure, a composite scaffold comprises: a microporous matrix having a multitude of interconnected pores collectively defining void space opening to an exterior surface of the microporous matrix; and a structure supporting the microporous matrix; the composite scaffold having a measurable dry weight value representing a weight of the composite scaffold in a substantially dry state, wherein the microporous matrix is less than approximately 6% of the dry weight value of the composite scaffold.

According to another aspect of the disclosure, a scaffold comprises: a three-dimensional support structure having a length dimension extending between first and second ends of support structure, the support structure comprising first and second outer layers spaced apart by a distance therebetween defining a thickness dimension normal to the length dimension, and a plurality of spacer elements connecting the first and second outer layers to maintain separation therebetween; wherein the thickness dimension of the support structure changes less than approximately 35% upon elongation of the length dimension by approximately 13%.

According to another aspect of the disclosure, a scaffold comprises: a three-dimensional support structure having a length dimension extending between first and second ends of support structure and defining a cross-sectional area normal to the length dimension, the support structure comprising first and second outer layers spaced apart to define an interior space volume therebetween, and a plurality of spacer elements extending through the interior space volume between the first and second layers and attached therebetween to maintain separation of the first and second layers;

wherein the cross-sectional area changes less the approximately 5% upon elongation of the length dimension by approximately 13%.

According to another aspect of the disclosure, a scaffold comprises: a three-dimensional support structure having a length dimension extending between first and second ends of support structure and defining a width dimension normal to the length dimension, the support structure comprising first and second outer layers spaced apart by a distance therebetween defining a thickness dimension normal to the length dimension and the width dimension, and a plurality of spacer elements connecting the first and second outer layers to maintain separation therebetween; wherein the width dimension of the support structure changes less than approximately 5% upon elongation of the length dimension by approximately 13%.

According to another aspect of the disclosure, a scaffold structure comprises: first and second outer layers having length dimensions defined by respective first and second ends thereof and defining an interior space therebetween, each of the first and second outer layers comprising a plurality of interconnected wales extending substantially parallel to the respective length dimensions; a plurality of spacer elements extending substantially normal to the respective length dimensions through the interior space and attached to each of the first and second outer layers proximate one of the plurality of wales, the plurality of spacer elements at least partially partitioning the interior space into a plurality of channels extending along the respective length dimensions of the first and second outer layers.

According to another aspect of the disclosure, a composite scaffold having a measurable volume comprises: a microporous matrix having a multitude of interconnected pores opening to an exterior surface of the microporous matrix and collectively defining void space, wherein the composite scaffold has a density of approximately between 0.05 g/cc and 0.75 g/cc, wherein the density is defined as the mass per unit volume of the composite scaffold.

According to another aspect of the disclosure, a composite scaffold having a measurable volume comprises: a microporous matrix having a multitude of interconnected pores collectively defining void space opening to an exterior surface of the microporous matrix; and a structure supporting the microporous matrix; wherein the composite scaffold has a ratio of total surface area to volume of approximately between 160,000:1 and 190,000:1, wherein the ratio defines the surface area of the scaffold to the volume the composite scaffold excluding the void space.

According to another aspect of the disclosure, a scaffold comprises: a three-dimensional support structure extending along an axis between first and second ends of support structure, the support structure comprising first and second layers spaced apart to define an interior space volume therebetween, and a plurality of spacer elements extending through the interior space volume between the first and second layers and attached therebetween to maintain separation of the first and second layers and defining a cross-sectional normal the axis; and a microporous matrix in the interior space and having a multitude of interconnected pores collectively defining void space between first and second ends of the support structure; wherein at least approximately 60% of the void space comprises pores having a size dimension of at least 10 μm or greater; and wherein a volume of the void space is between approximately 3.0 cm$^3$/gram and 9.0 cm$^3$/gram.

According to another aspect of the disclosure, a composite scaffold comprises: a microporous matrix having a multitude of interconnected pores opening to an exterior surface of the microporous matrix and collectively defining void space; and a structure supporting the microporous matrix; the composite scaffold having a substantially rectangular cross-section defined by exterior sides wherein a plurality of the interconnected pores are open to one of the exterior sides and have a largest dimension oriented relative to the one exterior side. In one embodiment, the plurality of the interconnected pores have a largest dimension oriented between approximately between 45° and 135° relative to the one exterior side.

According to another aspect of the disclosure, a scaffold comprises: a three-dimensional support structure having a length dimension defined by first and second ends thereof and a thickness dimension, normal to the length dimension, defined by first and second outer layers separated by a space, and a plurality of spacer elements extending through the space and connecting the first and second outer layers; wherein the void space surface area to measurable volume is between approximately 500 cm$^2$/cm$^3$ and 7,000 cm$^2$/cm$^3$ According to another aspect of the disclosure, a composite scaffold occupying a measurable volume and comprises: a microporous matrix having a multitude of interconnected pores collectively defining void space having a surface area; and a structure supporting the microporous matrix; wherein the void space surface area to measurable volume is between approximately 5,000 cm$^2$/cm$^3$ and 16,000 cm$^2$/cm$^3$ According to another aspect of the disclosure, a composite scaffold comprising: a microporous matrix having a multitude of interconnected pores opening to an exterior surface of the microporous matrix and collectively defining void space; and a structure supporting the microporous matrix; herein a surface area of the composite scaffold is between approximately 0.3 m$^2$/gram and 15 m$^2$/gram.

According to another aspect of the disclosure, a method of ligament or tendon injury repair with a composite scaffold comprises: A) providing a composite scaffold comprising: i) first and second layers spaced apart to define an interior space therebetween and a plurality of spacer elements extending through the interior space and attached to the first and second layers; and ii) a microporous matrix having a multitude of interconnected pores disposed within the interior space, and B) pre-tensioning the composite scaffold along a length dimension thereof; C) attaching the composite scaffold to an allograft or autograft tendon or a damaged or torn ligament or tendon.

According to another aspect of the disclosure, a method of making a composite scaffold comprises: A) constructing a three-dimensional support structure extending along a length dimension between first and second ends thereof and defining an interior space within the support structure; and B) forming a microporous matrix within the interior space, the microporous matrix having a multitude of interconnected pores in fluid communication with exterior surfaces of the support structure, wherein a plurality of the interconnected pores are oriented relative to the dimensional characteristics of the support structure. In embodiments, the plurality of interconnected pores are oriented radially inward into the interior space from exterior surfaces of the support structure. In embodiments, the plurality of interconnected pores are oriented towards the length dimension of the support structure.

According to another aspect of the disclosure, a composite scaffold comprises: a support structure having an exterior profile defining an interior space and extending along a length dimension between first and second ends thereof; a microporous matrix disposed within the interior space having a multitude of interconnected pores opening exteriorly of the support structure; wherein a plurality of the interconnected pores are oriented relative to the dimensional characteristics of the support structure.

According to another aspect of the disclosure, a composite scaffold comprises: a microporous matrix having a multitude of interconnected pores collectively defining void space opening to an exterior surface of the microporous matrix; and a structure supporting the microporous matrix; the composite scaffold having a measurable dry weight value representing a weight of the composite scaffold in a substantially dry state, wherein the microporous matrix is less than approximately 6% of the dry weight value of the composite scaffold.

In embodiments, the second support matrix, e.g. the sponge, degrades between approximately two to twelve times faster than the first support matrix based on either mass loss or molecular weight loss. The composite scaffold may have a degradation profile with greater than or equal to 50% strength retention for at least approximately two weeks after implantation and a mass loss of 100% mass loss between approximately six and twelve months or longer after implantation.

In embodiments, a higher density or mass of the support matrix provides the primary and bulk structure of the disclosed scaffold, in comparison to the more porous matrix disposed therein. More specifically, the first and second support matrixes have different densities or mass components relative to each other. In one embodiment, the first support matrix, e.g., the textile, has a measurable mass or density which is greater than or equal to one times that of the mass or density of the second support matrix, e.g. the sponge.

In the disclosed embodiment, the pore structure of the microporous matrix is designed to facilitate cellular attachment, proliferation, and ingrowth throughout the scaffold dimensions. In embodiments, the faces of the device, the secondary matrix, or pore structure could be engineered in architecture to encourage cellular migration in a certain direction, or to encourage the formation of aligned tissues such as connective tissues. In other embodiments the surfaces of the device might differ from each other in physical or chemical characteristics to reflect use in specific anatomic locations—i.e. one side to encourage integration with bone while the other to encourage tendon; or one side to encourage abdominal wall regeneration but the other side to prevent adhesions of internal organs.

In embodiments, the composite scaffold disclosed herein provides a measurably high surface area to volume ratio, compared to existing commercially available devices, to facilitate more rapid and greater quantity of cell infiltration and tissue ingrowth within the composite scaffold. More specifically, based predominantly on the first support matrix, e.g., the textile, surface area of the fiber to volume of the device ratio, calculated using scaffold denier, polymer density and dimensions, greater than 10 times.

In embodiments, the scaffold may have ends that narrow and transition into suture-like dimensions or are modified, e.g. stitched or knotted, to attach to conventional suture used in the procedures described herein. In other embodiments, the first support matrix, e.g., the textile, has ends or edges that are modified to be heat set or embroidered or impregnated with other materials to facilitate better handling, better integration with existing tissue and to further reduce dimensional distortion of the scaffold under pressure, tensile, or shear forces. In other embodiments, a monofilament or multifilament suture of any material may pass through the scaffold lengthwise and exit both ends, and be attached or fixed to the scaffold.

In other embodiments selected sections of the scaffold may be repeated, either randomly or with fixed frequency to increase or decrease the density of the scaffold by increasing or decreasing the density of the textile, for example, by a change in the textile pattern of the first support matrix. In still other embodiments, such repeating regions may be chosen to alter the surface finish of the scaffold by altering the smoothness or roughness, of the exterior surface of the scaffold to enhance acceptance of the scaffold once implanted.

In one embodiment, the composite scaffold comprises just a single three-dimensional support matrix which may be the same or different than either of the first or second support matrices described herein and may have any of the characteristics of the composite scaffold described herein.

Also disclosed is a method of treatment of ligament or tendon injury wherein a scaffold is attached to an allograft or autograft tendon and used to replace a damaged ligament or tendon, or, the scaffold is used to augment a damaged or torn ligament or tendon. Methods of use may include preparation of the scaffold with a solution to enhance its performance, pretensioning of the scaffold, and/or fixing the femoral end and independently tensioning and fixing a tendon and graft in the tibial tunnel.

In use, the composite scaffold may be utilized in a wide array of medical procedures including to reinforce a suture repair, stand alone repair or reconstruction, or reconstruction using a tissue graft and for fixation purposes. Reinforcement of a repair or reconstruction using the composite scaffold may be applicable to the knee, ankle, shoulder, hip, elbow, foot, and hand, and non-musculoskeletal soft tissue.

In accordance with another aspect of the disclosure, a graft preparation table provides a surface and fixation mechanisms that allow for independent tensioning of tissue, e.g. tendon or ligament, and composite scaffold either prior to or during an implantation procedure.

In accordance with another aspect of the disclosure, a fixation device allows tissue, e.g. tendon or ligament, and composite scaffold to be attached to each other avoiding the need for whip stitching. Such device may comprise a clip with legs that go through graft and tendon.

DESCRIPTION THE DRAWINGS

The various features and advantages of the present invention may be more readily understood with reference to the following detailed description taken in conjunction with the accompanying drawings, wherein like reference numerals designate like structural elements, and in which.

Figure 1A:
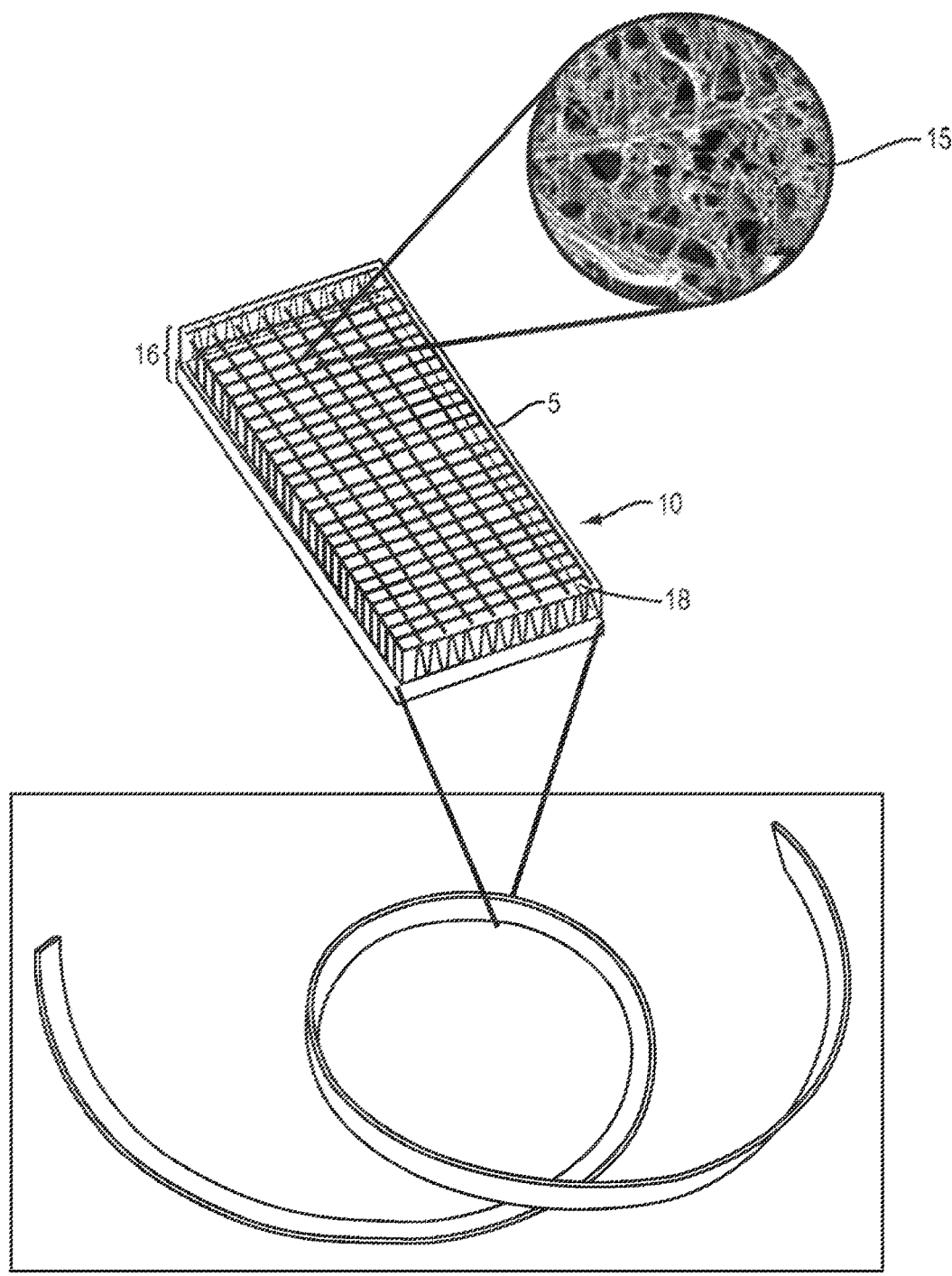
FIG. 1A is a conceptual illustration of a composite scaffold in accordance with the disclosure.
Figure 1B:
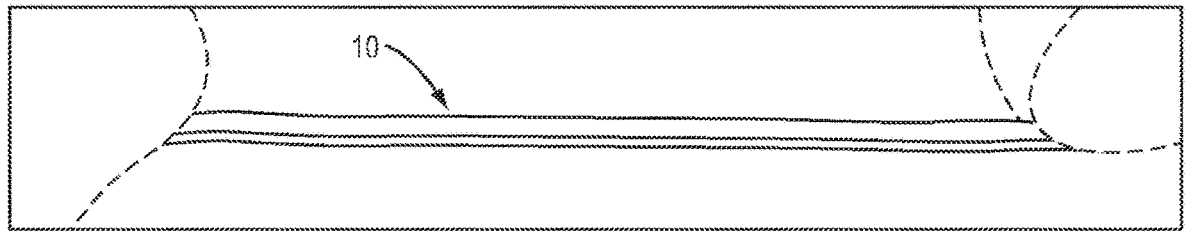
FIG. 1B is a photograph of a composite scaffold in accordance with the disclosure.
Figure 1C:
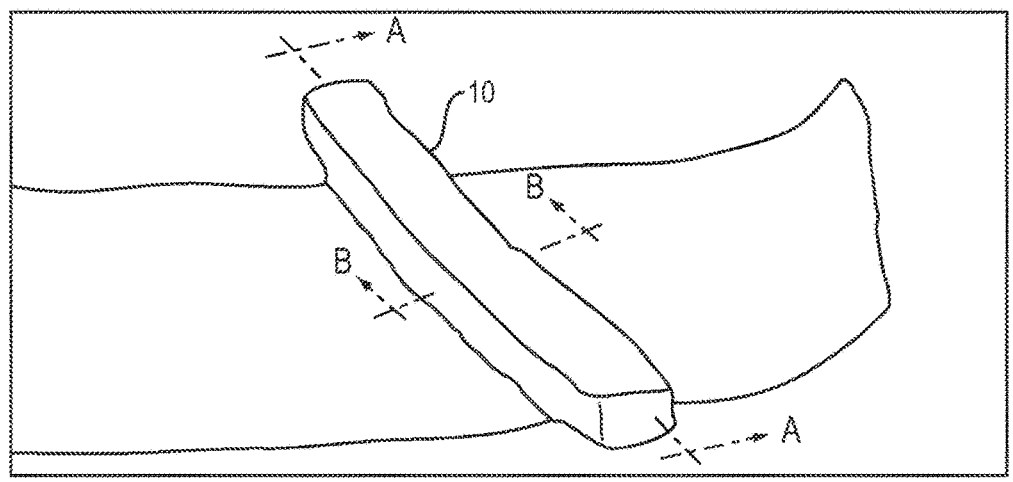
FIG. 1C is a photograph of a composite scaffold in accordance with the disclosure.
Figure 5A:
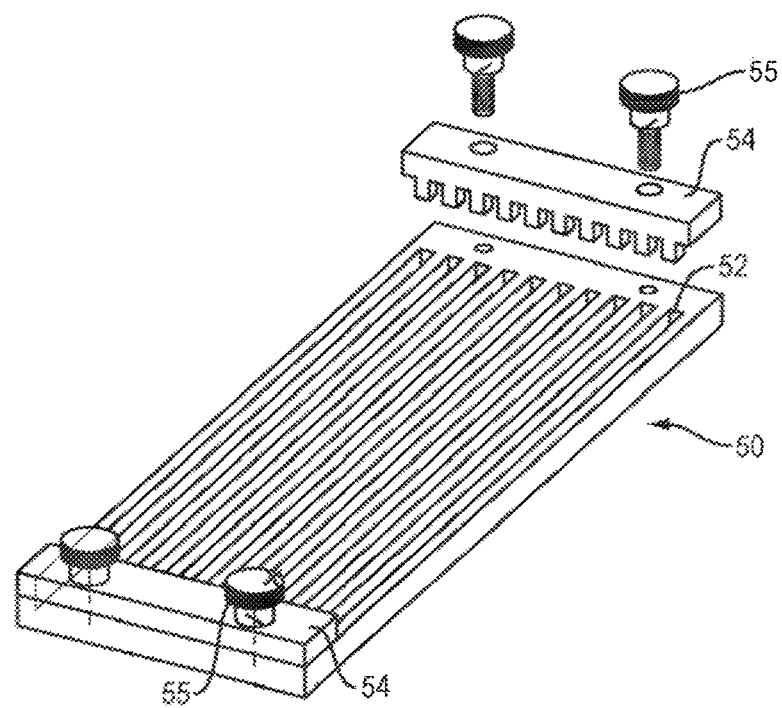
FIG. 5A is a perspective view of a mold useful in making a composite scaffold in accordance with the disclosure.
Figure 5B:
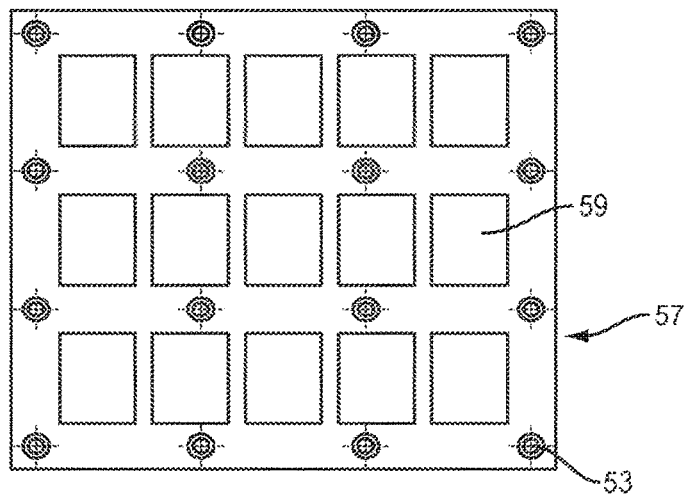
Figure 5C:
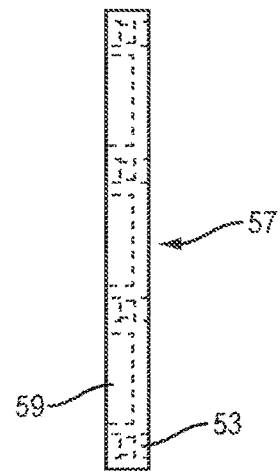
Figure 5D:
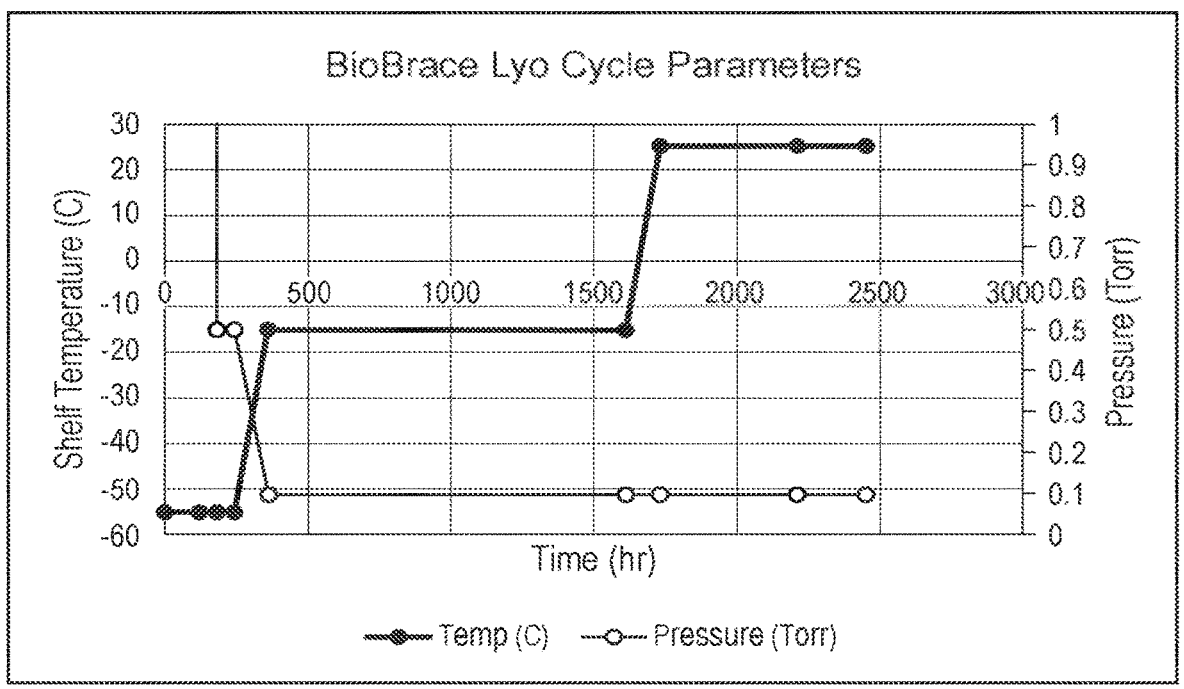
Figure 6A:
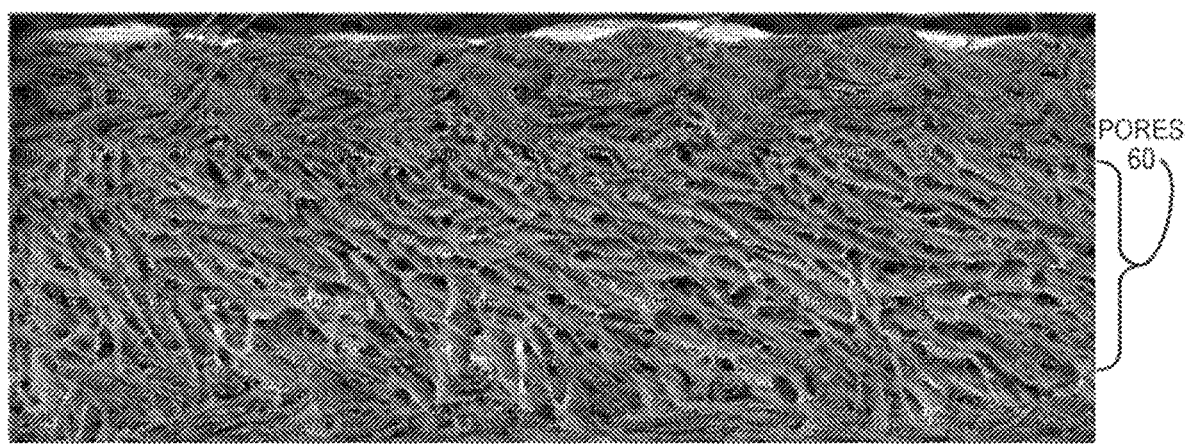
Figure 6B:
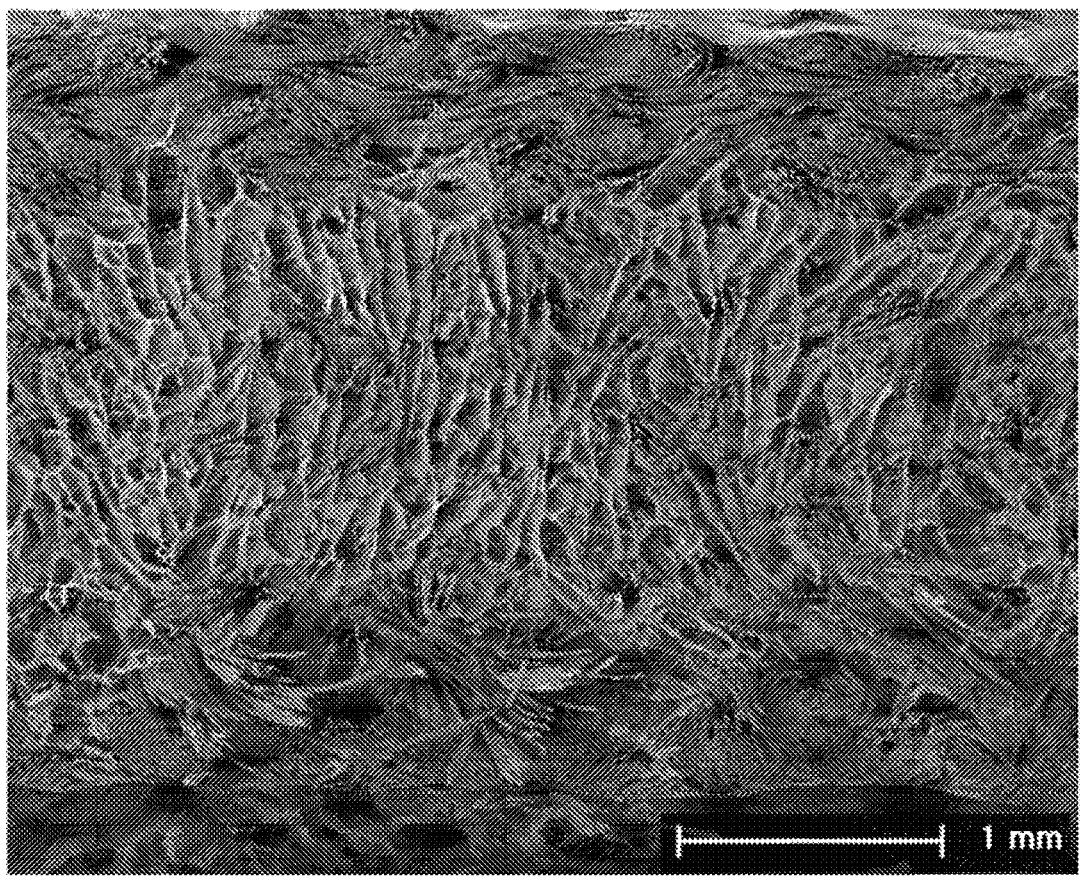
Figure 6C:
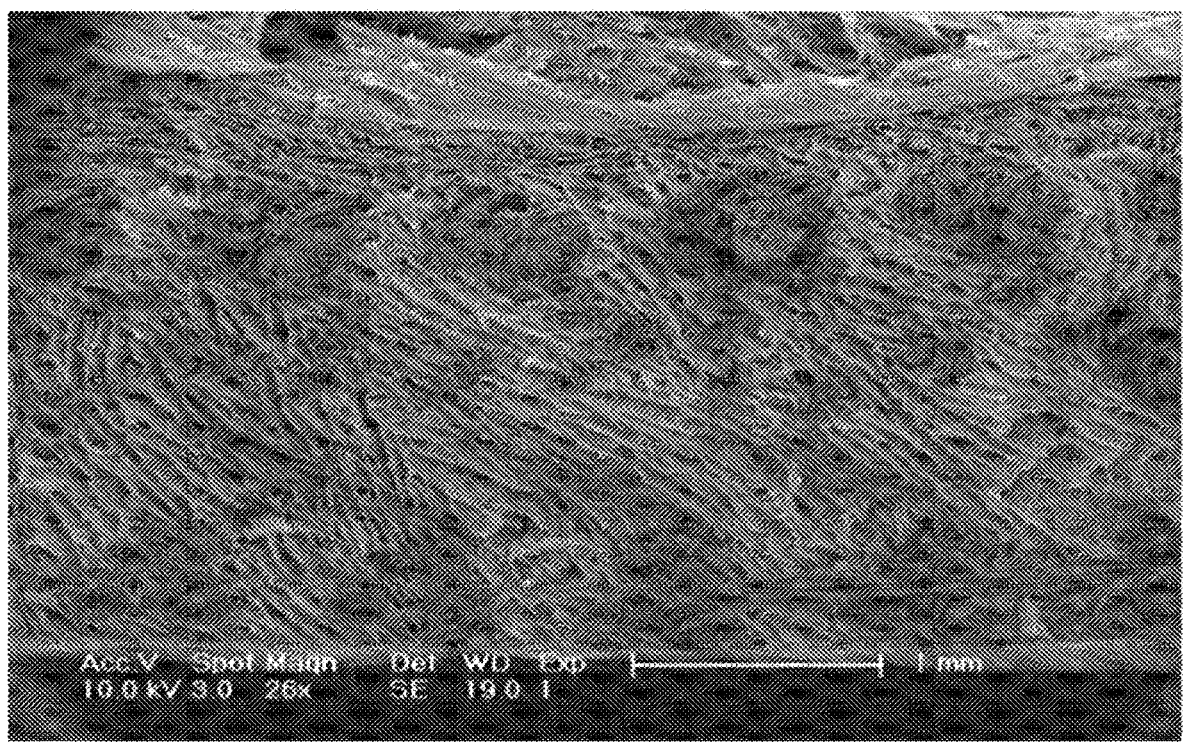
Figure 6D:
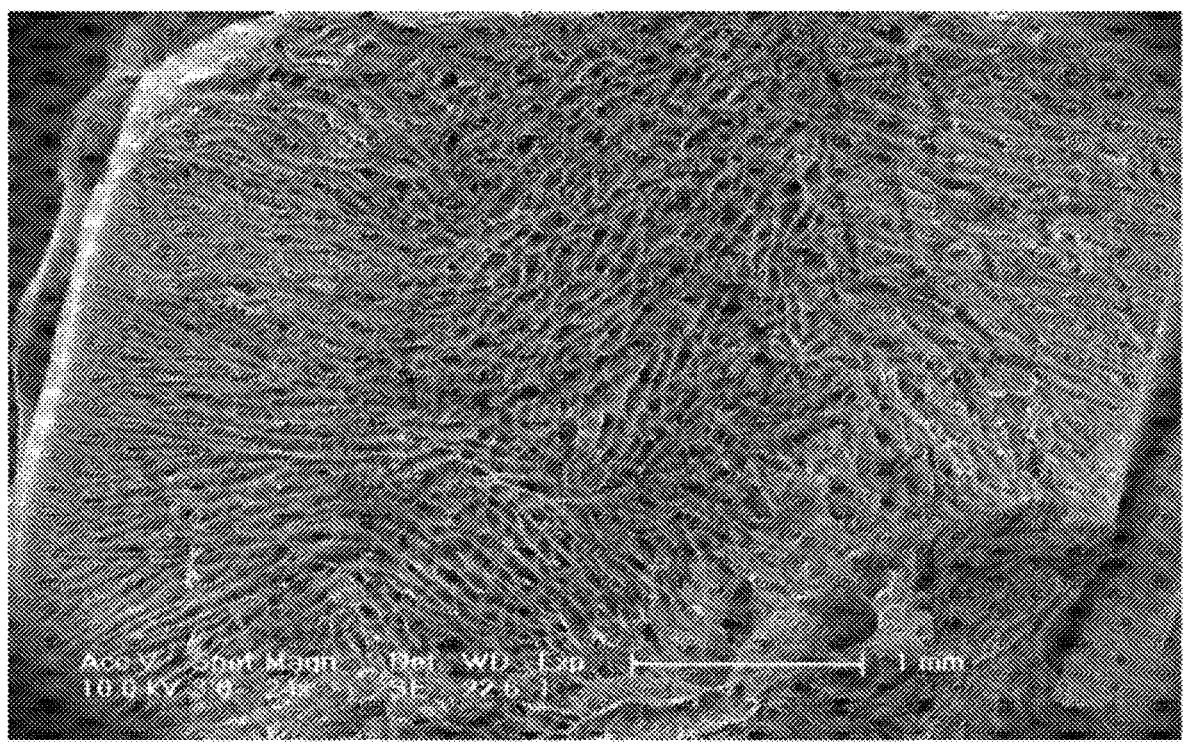
Figure 6E:
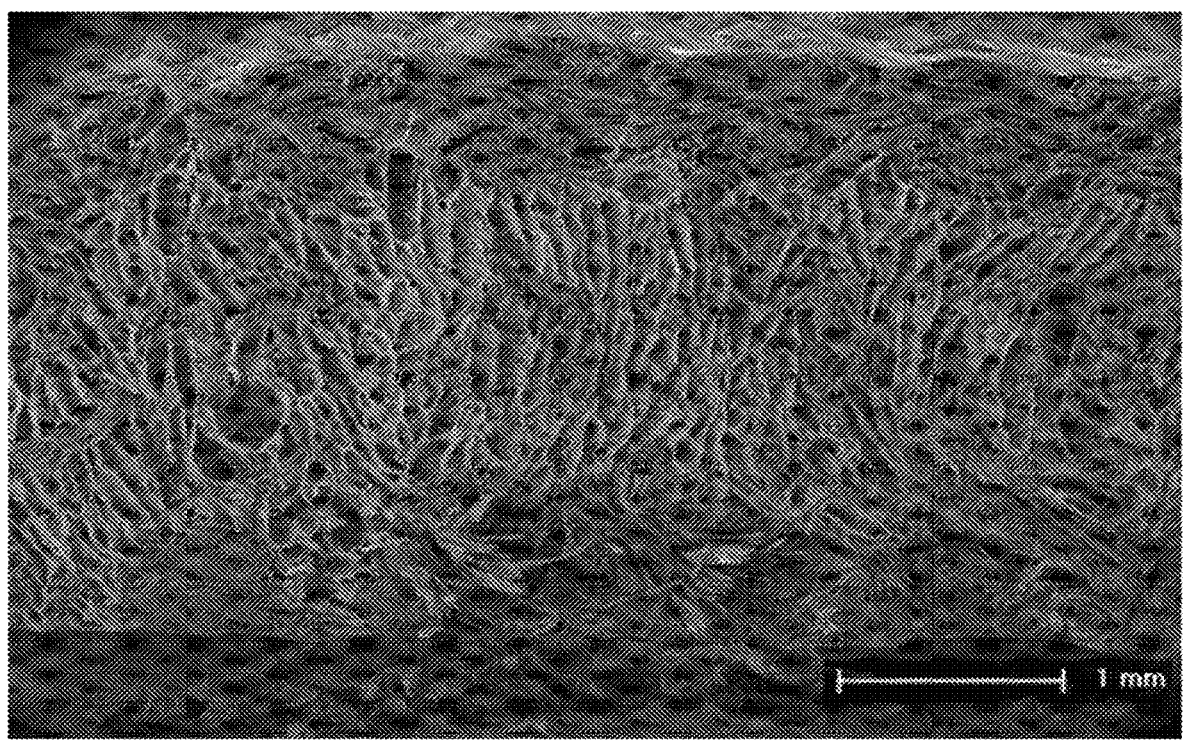
Figure 6F:
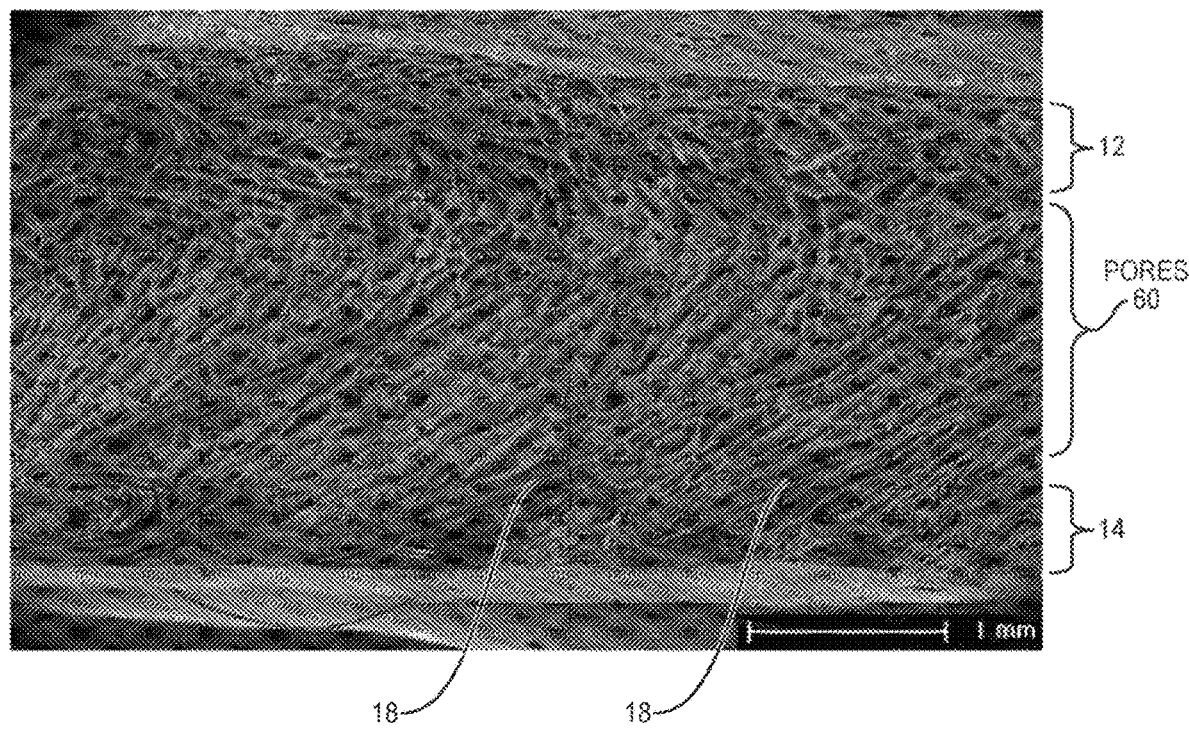
Figure 6G:
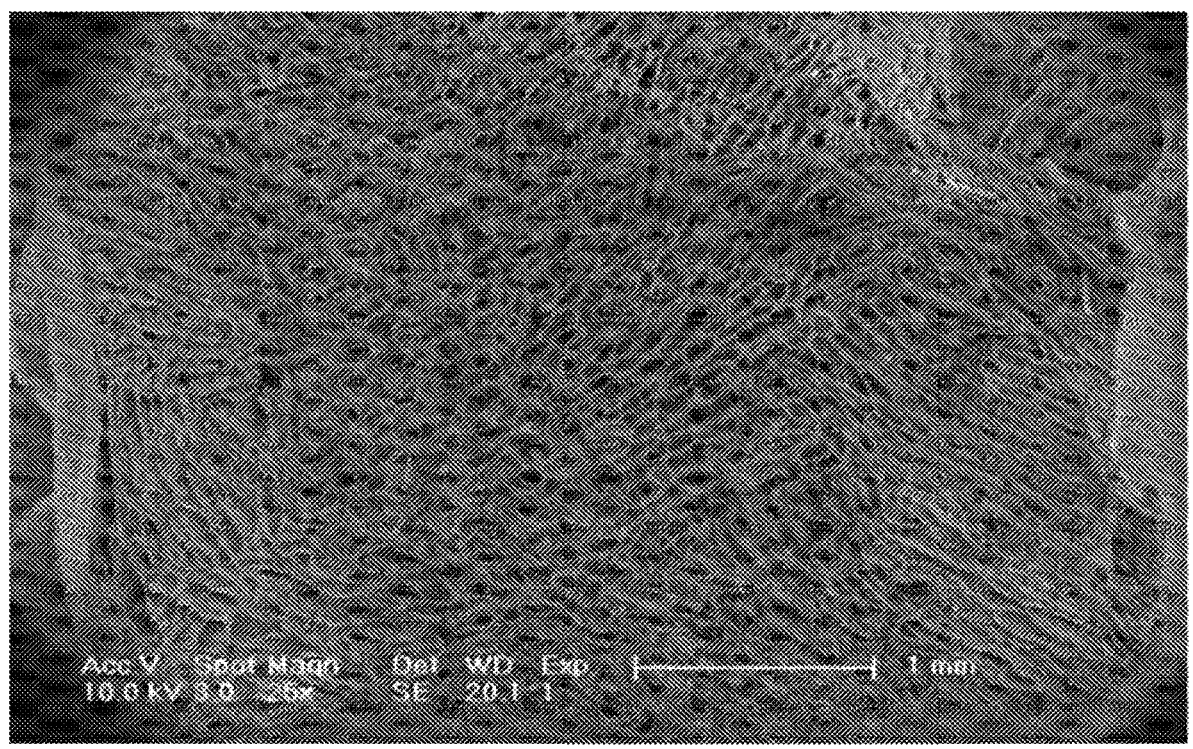
Figure 6H:
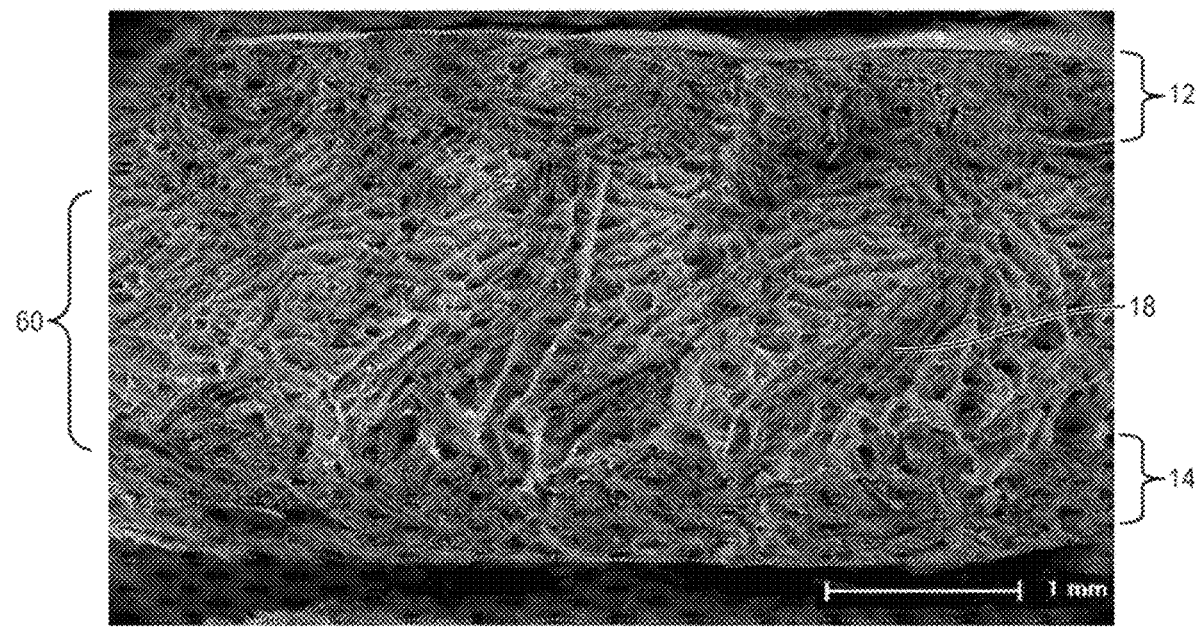
Figure 6I:
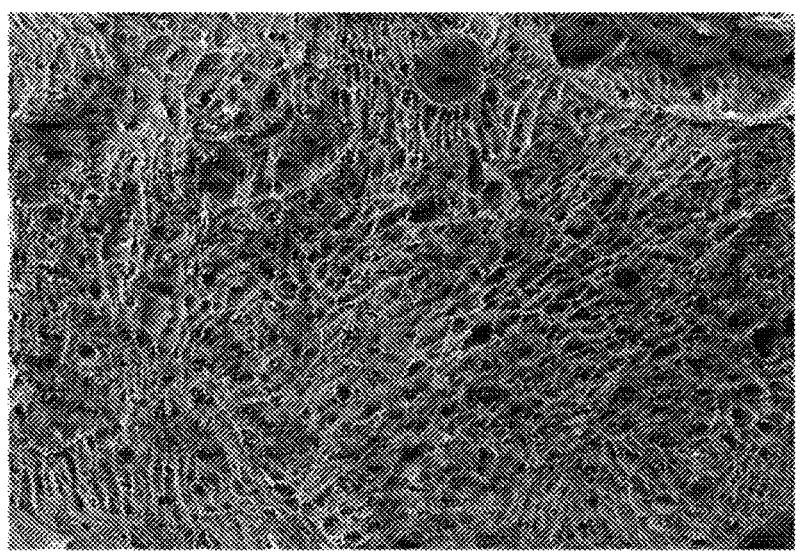
Figure 7A:
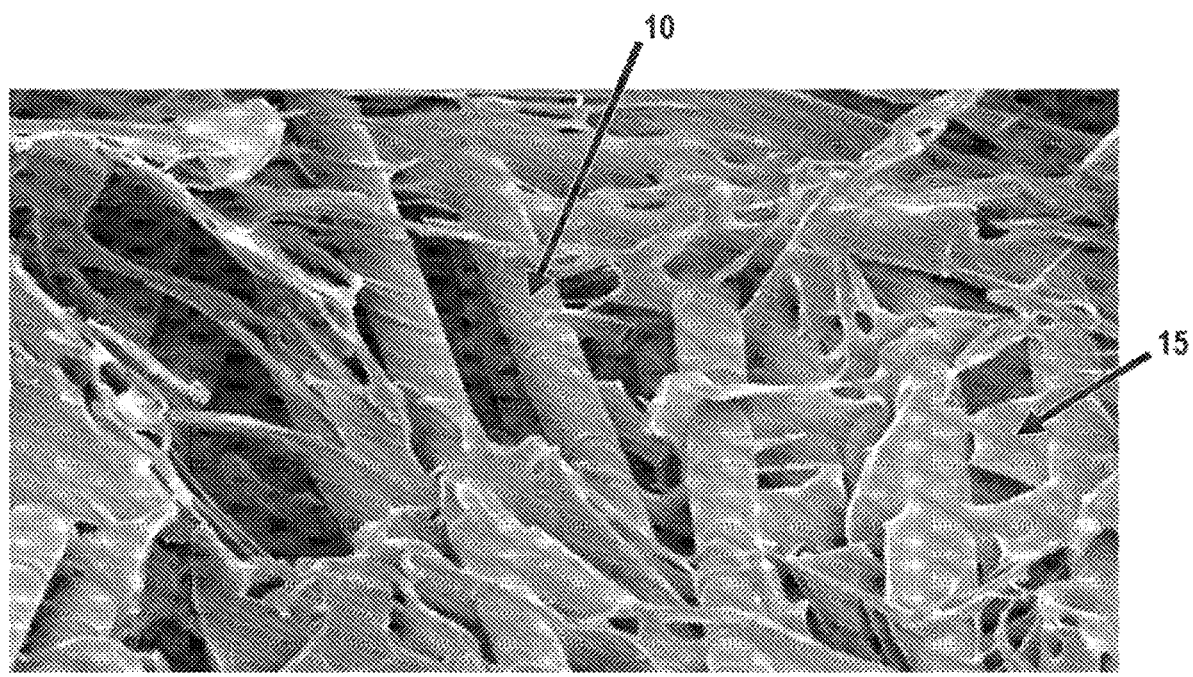
Figure 7B:
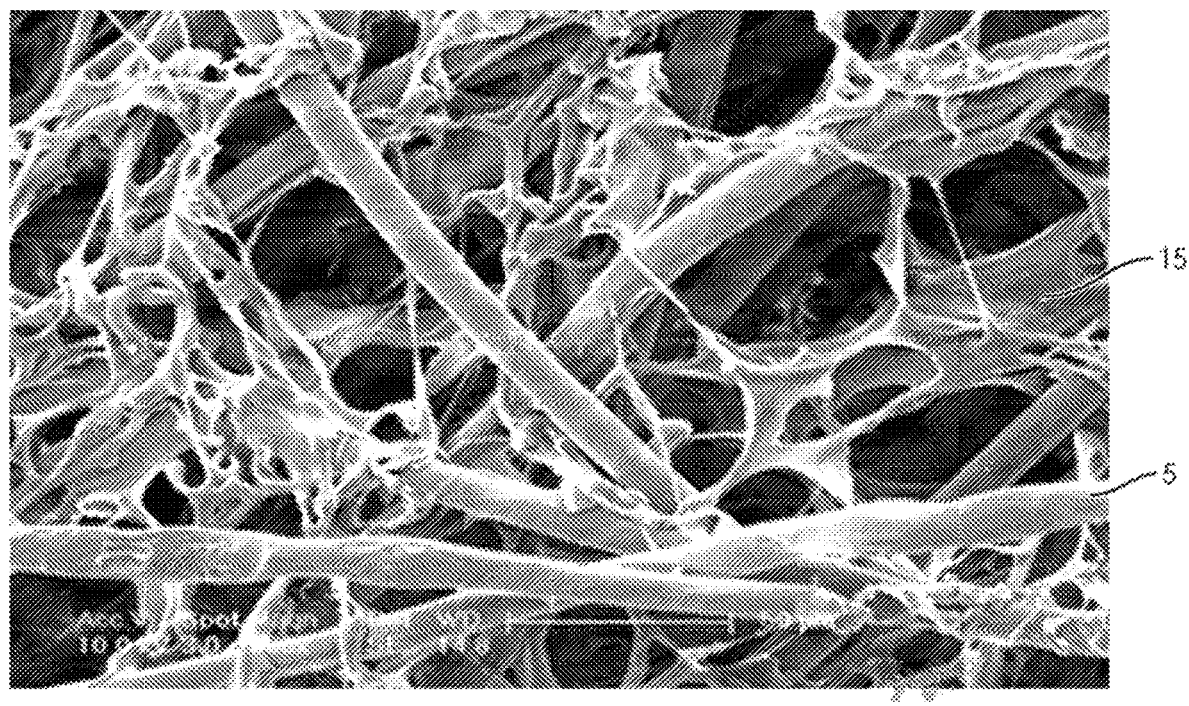
Figure 7C:
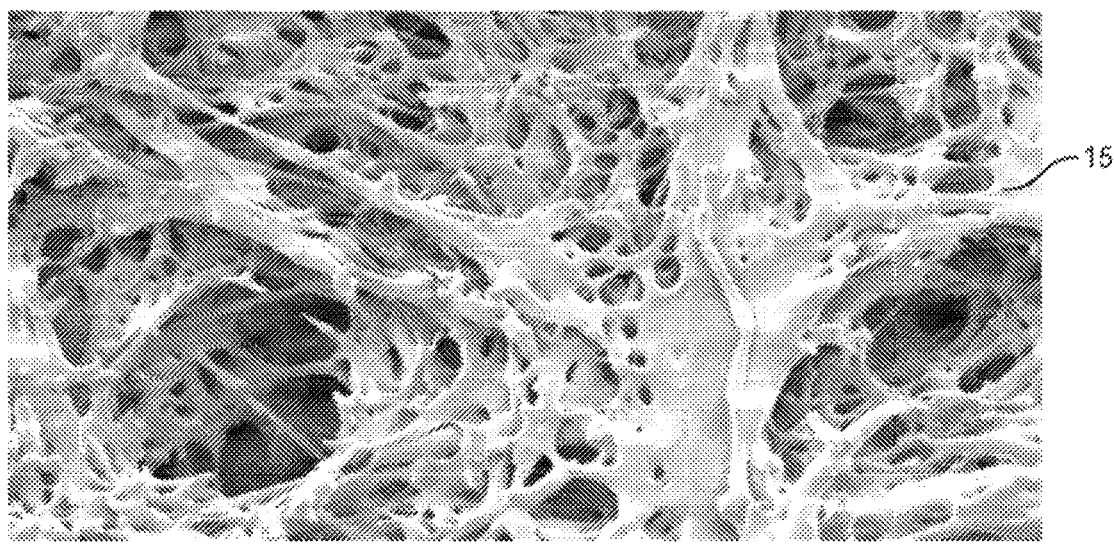
Figure 8:
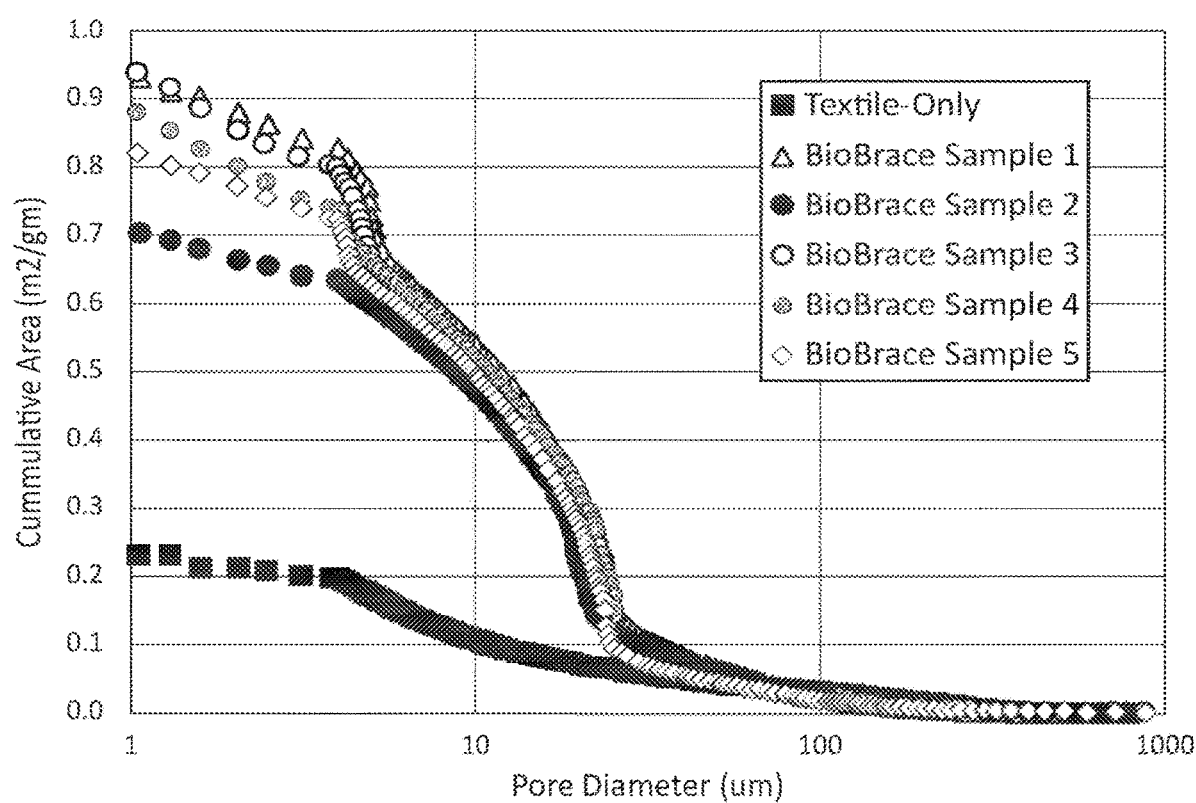
Figure 9:
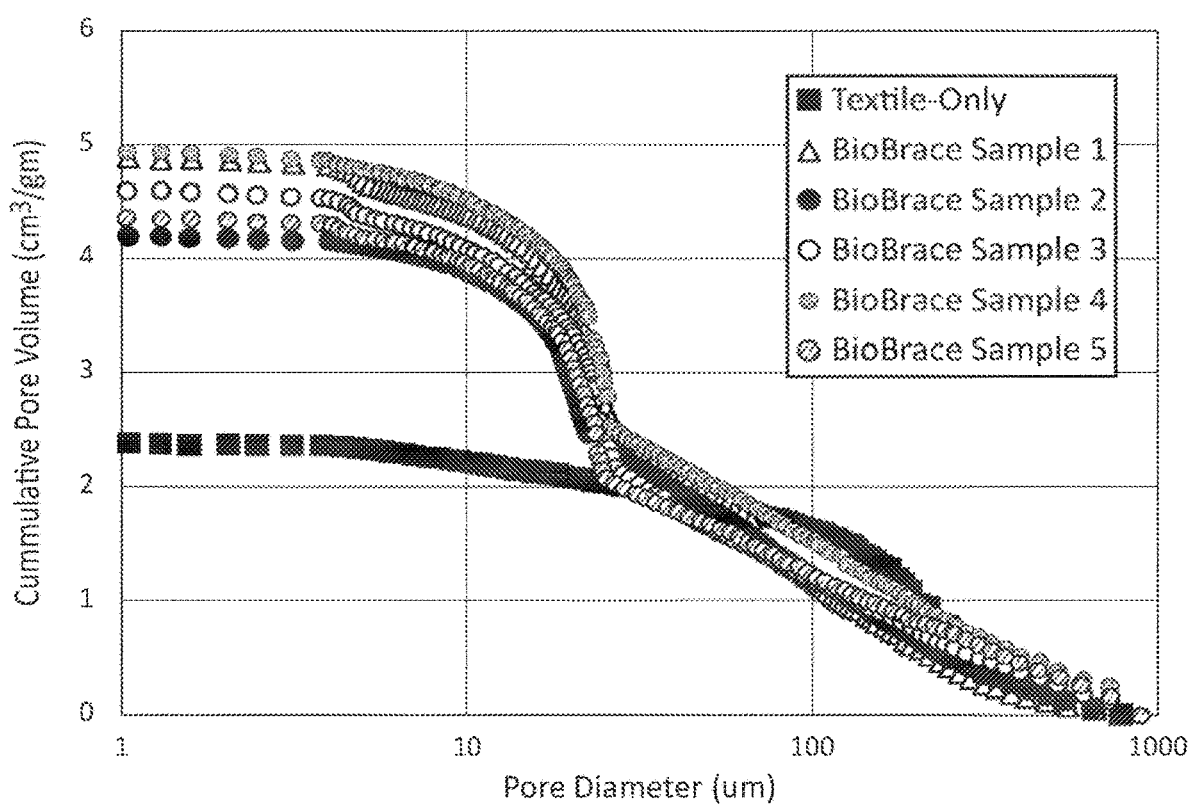
Figure 10:
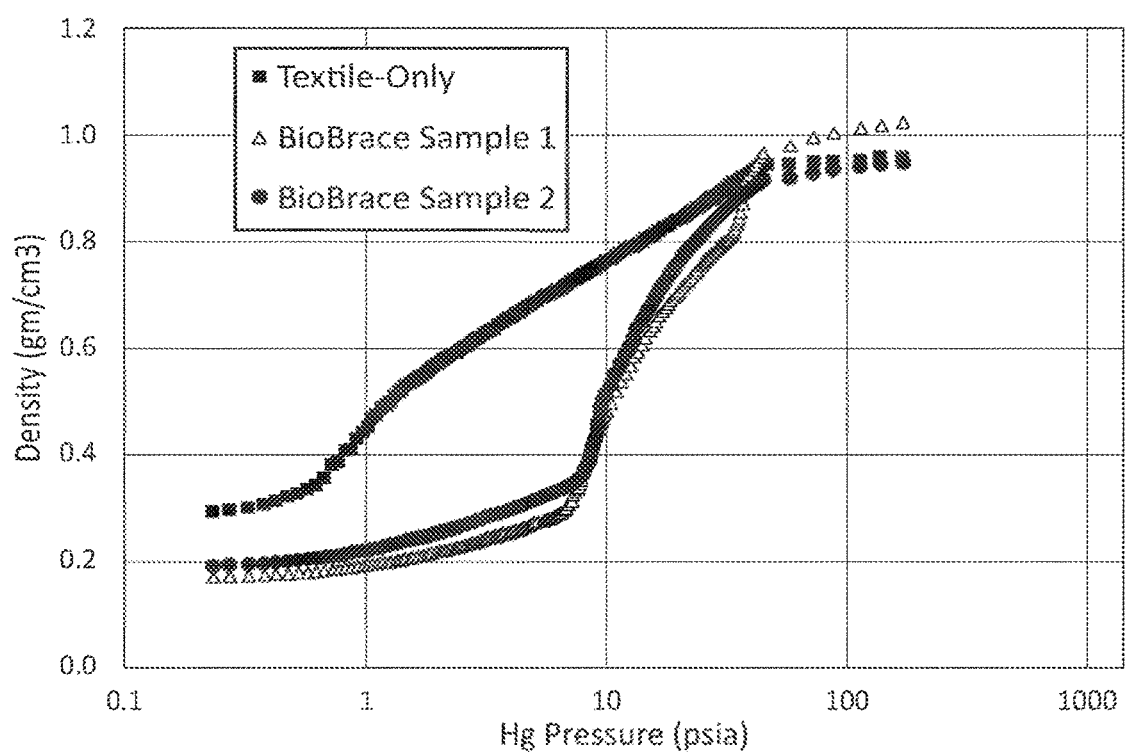
Figure 11:
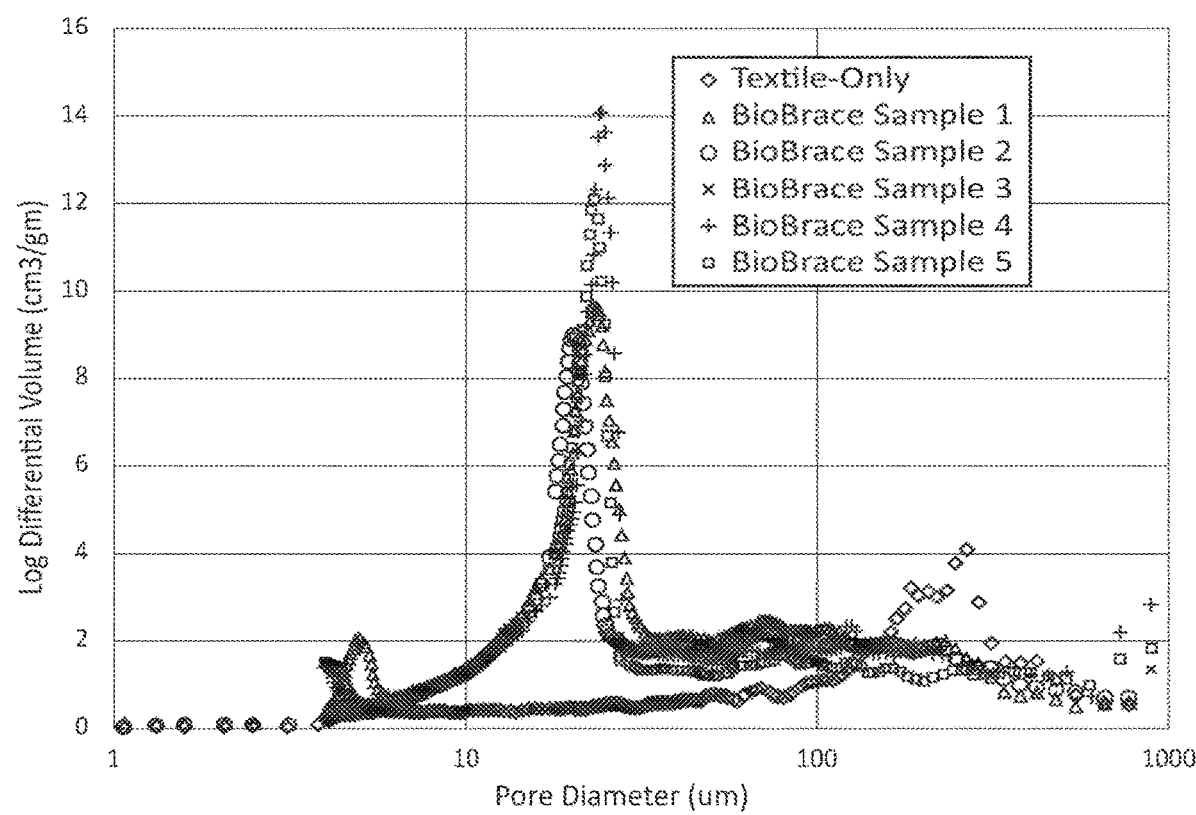
Figure 12:
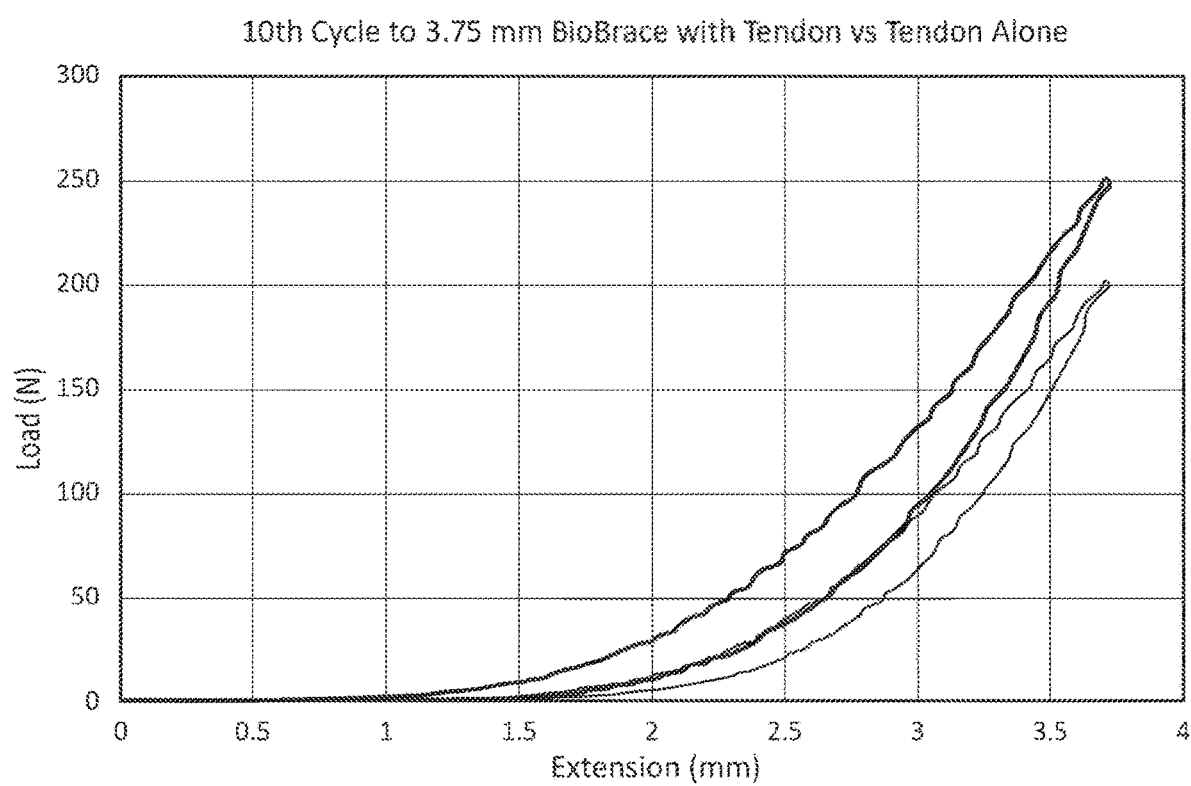
Figure 13A:
Figure 13B:
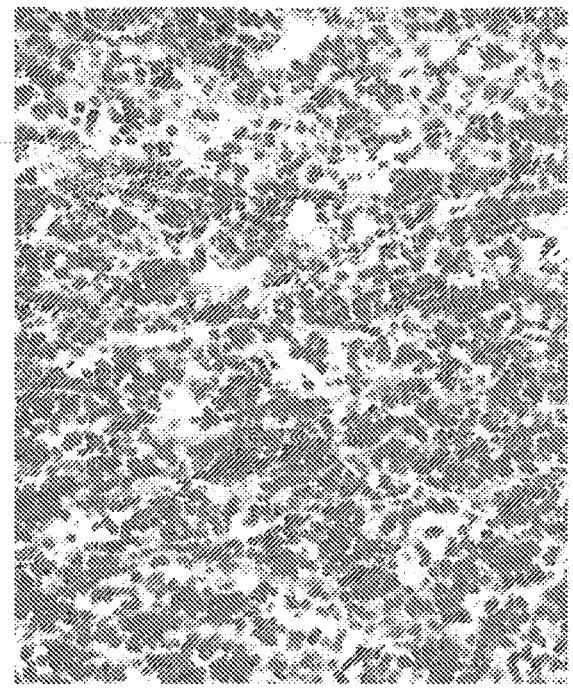
Figure 14:
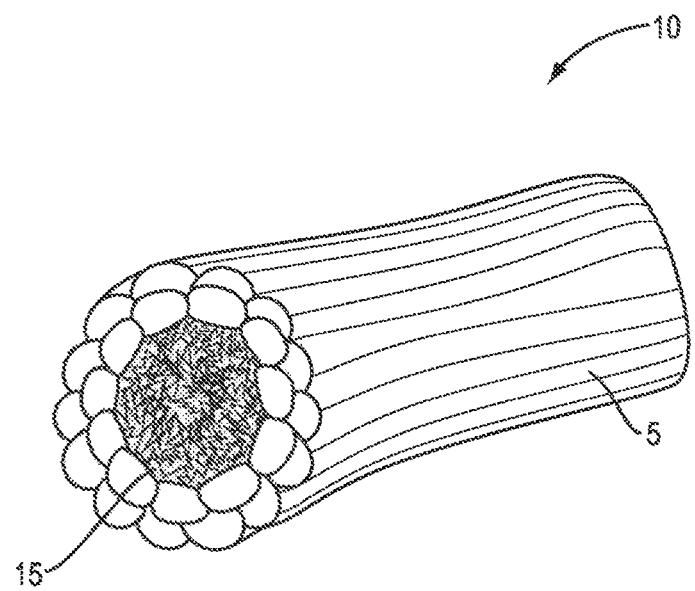
Figure 15:
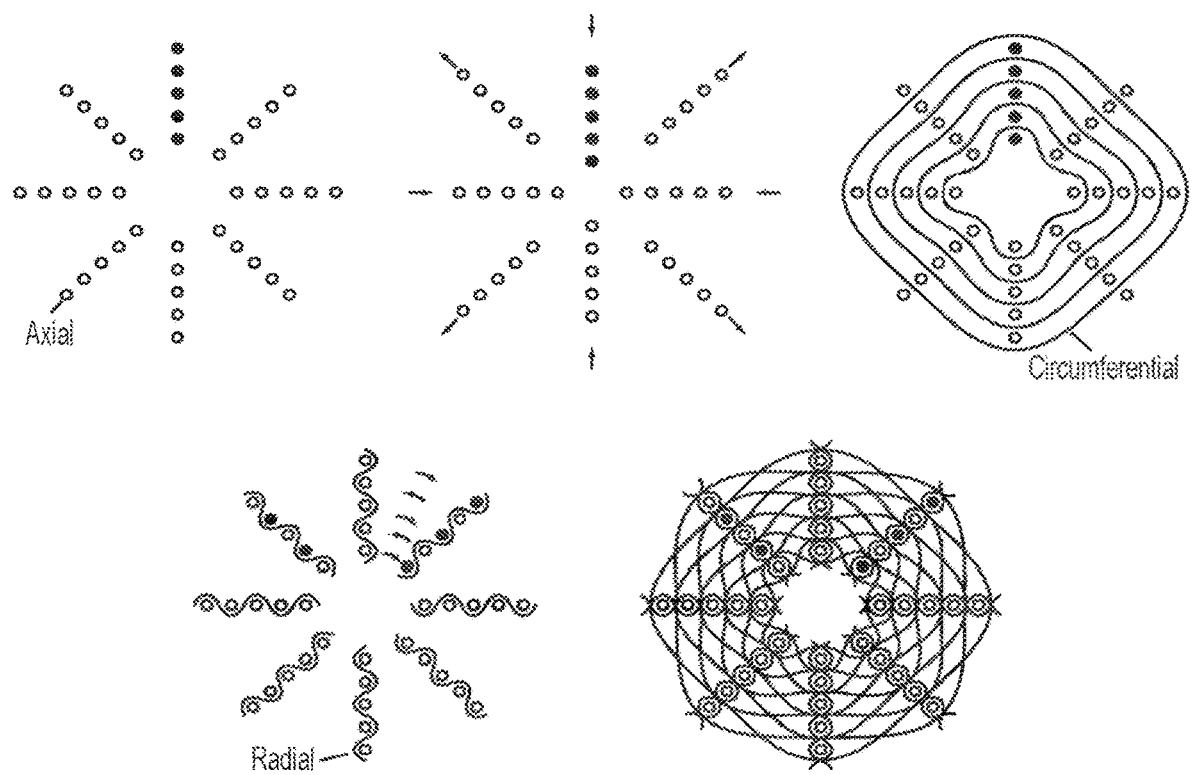
Figure 16:
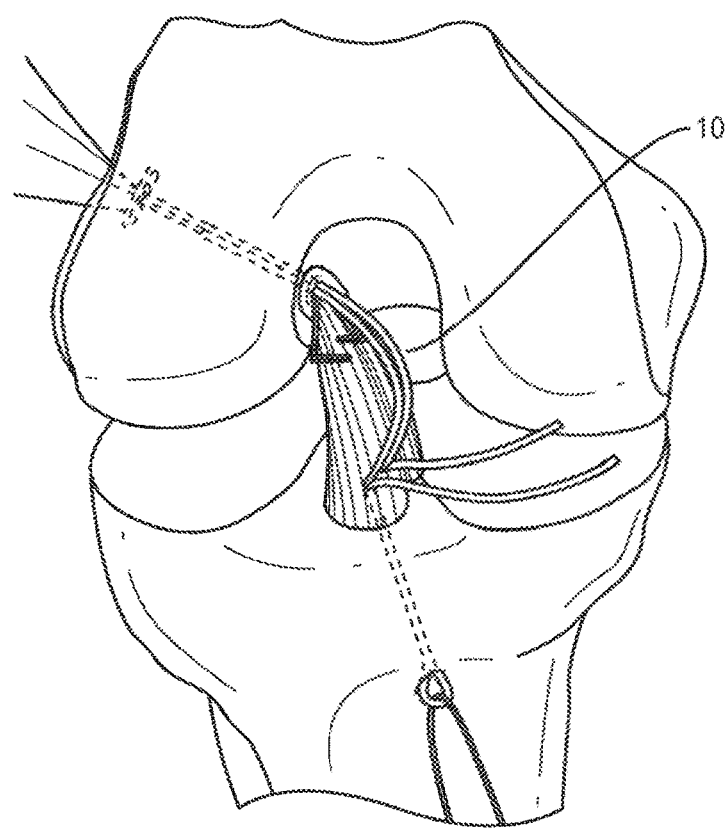
Figure 17:
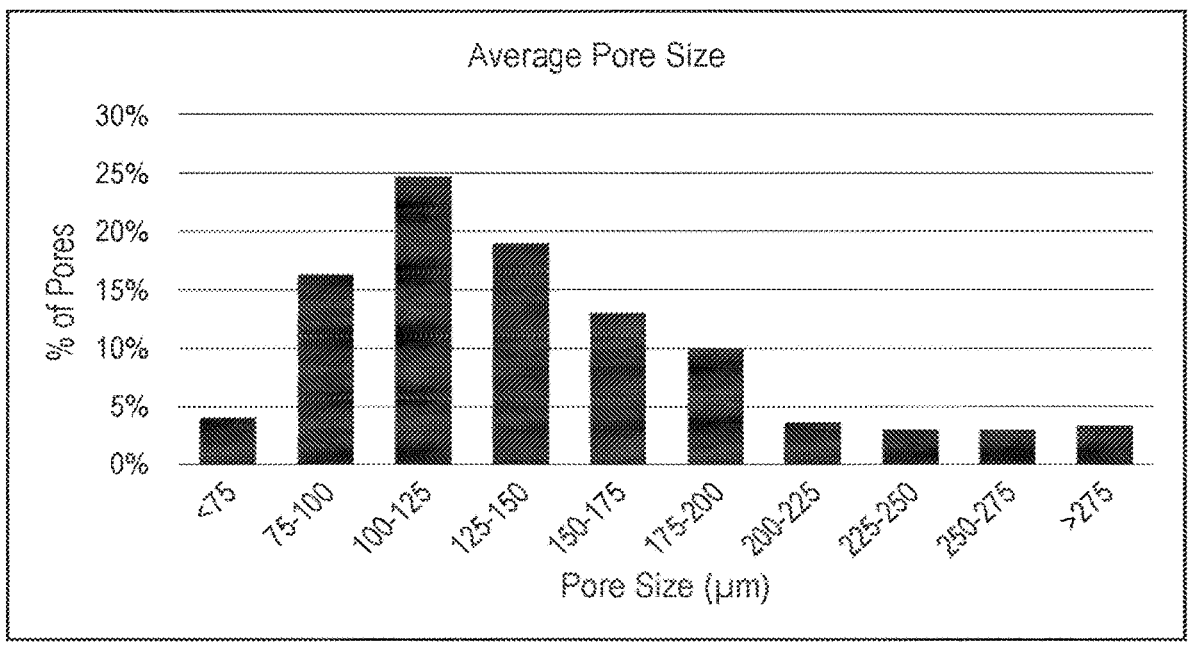

FIGS. 5B-C are top and side plan views, respectively, of another mold useful in making a composite scaffold in accordance with the disclosure;

FIG. 5D illustrates graphically the relationship of temperature, time and pressure during the lypholization process in accordance with the disclosure;

FIGS. 6A-6C are SEM photograph of a sagittal cross-sectional view of the microporous matrix of the composite scaffold of FIG. 1C as taken along line A-A within the in accordance with the disclosure;

FIG. 6D is an SEM photograph of a coronal cross-sectional view of the microporous matrix of the composite scaffold of FIG. 1C as taken along line B-B within the in accordance with the disclosure;

FIG. 6E is an SEM photograph of a transverse cross-sectional view of the microporous matrix of the composite scaffold of FIG. 1C as taken along line B-B within the in accordance with the disclosure;

FIG. 6F is an SEM photograph of a sagittal cross-sectional view of the microporous matrix of the composite scaffold of FIG. 1C as taken along line A-A within the in accordance with the disclosure;

FIG. 6G is an SEM photograph of a coronal cross-sectional view of the microporous matrix of the composite scaffold of FIG. 1C as taken along line B-B within the in accordance with the disclosure;

FIG. 6H is an SEM photographs of a transverse cross-sectional view of the microporous matrix of the composite scaffold of FIG. 1C as taken along line B-B within the in accordance with the disclosure;

FIG. 6I is an SEM photographs of a sagittal cross-sectional view of the microporous matrix of the composite scaffold of FIG. 1C as taken along line A-A within the in accordance with the disclosure;

FIG. 7A is an SEM photograph of a typical microporous matrix attached to a fiber support structure of a composite matrix in accordance with the disclosure;

FIG. 7B is an SEM photograph of a typical microporous matrix attached to a fiber support structure of a composite matrix in accordance with the disclosure;

FIG. 7C is an SEM photograph of the exterior surface of the typical microporous matrix of a composite scaffold in accordance with the disclosure;

FIG. 8 illustrates graphically test data defining the relationship of the cumulative total pore surface area relative to pore diameter in accordance with the disclosure;

FIG. 9 illustrates graphically the relationship of the cumulative total pore volume relative to pore diameter for a number of composite scaffold samples as well as only the textile only support structure in accordance with the disclosure;

FIG. 10 illustrates graphically the relationship of the composite scaffold in relation to Mercury pressure for a number of composite scaffold samples as well as only the textile only support structure in accordance with the disclosure;

FIG. 11 illustrates graphically the relationship of the distribution of pore diameter relative to the logarithmic differential volume in accordance with the disclosure;

FIG. 12 illustrates graphically the relationship of load versus extension for both a solo tendon and a tendon augmented with a composite scaffold in accordance with the disclosure;

FIG. 13A is a cross sectional microscopic view of the composite scaffold of FIG. 1C illustrating the porous matrix relative to the support matrix in accordance with the disclosure;

FIG. 13B is a cross sectional microscopic view of the composite scaffold of FIG. 1C hydrated with blood and illustrating how red blood cells fully infiltrate a collagen sponge porous matrix in accordance with the disclosure;

FIG. 14 is a photograph of the composite scaffold for MPFL repair or reconstruction in accordance with the disclosure;

FIG. 15 illustrates conceptually lapsed image of a circular textile structure a circular textile structure in various stages of manufacture in accordance with the disclosure;

FIG. 16 illustrates conceptually how a disclosed composite may be utilized for augmented ACL repair, stabilization or reconstruction in accordance with the disclosure; and FIG. 17 illustrates graphically the relationship of the distribution of pore diameter relative to percentage of pores as measured in accordance with the disclosure.

DETAILED DESCRIPTION OF THE INVENTION

Embodiments of the systems and methods are now described in detail with reference to the drawings in which like reference numerals designate identical or corresponding elements in each of the several views. Throughout this description, the phrase "in embodiments" and variations on this phrase generally is understood to mean that the particular feature, structure, system, or method being described includes at least one iteration of the disclosed technology. Such phrase should not be read or interpreted to mean that the particular feature, structure, system, or method described is either the best or the only way in which the embodiment can be implemented. Rather, such a phrase should be read to mean an example of a way in which the described technology could be implemented, but need not be the only way to do so. Further, words denoting orientation such as "top", "bottom", "side", "lower" and "upper", and the like, as well as references on a specific axis in three-dimensional space are merely used to help describe the location of components with respect to one another. No words denoting orientation are used to describe an absolute orientation, i.e., where an "upper" part must always be on top.

Referring to FIGS. 1A-6D, a composite scaffold 10 comprises a first three-dimensional support matrix, and a second matrix integrally formed with one another to form the composite scaffold 10 which maximize the surface area to volume ratio and surface area per weight ratios of the scaffold. Referring to FIG. 1A, the first matrix, in embodiments, may be implemented with a support structure 5 comprising a first outer layer 12 and a second outer layer 14 spaced apart to define an interior void space 16 therebetween. A plurality of spacer elements 18 extend between first outer layer 12 and a second outer layer 14 to maintain separation of the layers. In embodiments, each of layers 12, 14, and spacer elements 18 may be implemented as a three-dimensional textile structure, each having different geometries, fibers, or material compositions. For example, any of outer layers 12, 14, and spacer elements 18 may be implemented with a textile of multifilament fibers and/or monofilament fibers. Support layers 12 and 14 may be implemented as substantially planar three dimensional textile comprising multi-layer knitted surfaces and spacer elements 18 may be implemented with interconnecting yarns in the "Z" direction normal to the planes of layers 12 and 14 provide support to prevent collapse.

The support structure 5 is intended to provide mechanical support to the growing neo tissue and to provide resistance to compression such that the area intended for new tissue formation is maintained during patient movement and activity. As such the support structure 5 provides extensional strength in its long axis and stiffness to resist compression in the "z direction".

In embodiments, support structure 5 may be formed from any of 30-150 denier multifilament fiber, 30-150 denier monofilament fiber, or 30-150 denier composite yarn, or any combination thereof, e.g., a combination of multifilament and monofilament fibers, and may be optionally coated with an anti-adhesion material. Unfinished edges of the scaffold 10 maybe sealed or secured using methods inclusive, but not limited to, heat setting or embroidery. In one embodiment, support structure 5 is fabricated from 75-denier 30-filament Poly-L-Lactic Acid (PLLA) with a polymer density of 1.25 g/cc. Yarns may be braided over a twisted fiber yarn to provide higher stiffness yarns for use as a lay in as described below.

Figure 2A:
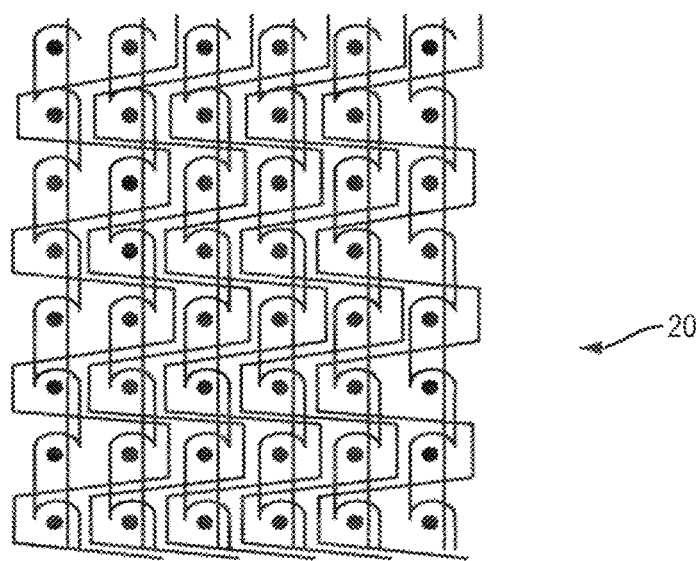
FIG. 2A is a conceptual illustration of knit pattern usable for exterior layers of the composite scaffold in accordance with the disclosure.
Figure 2B:
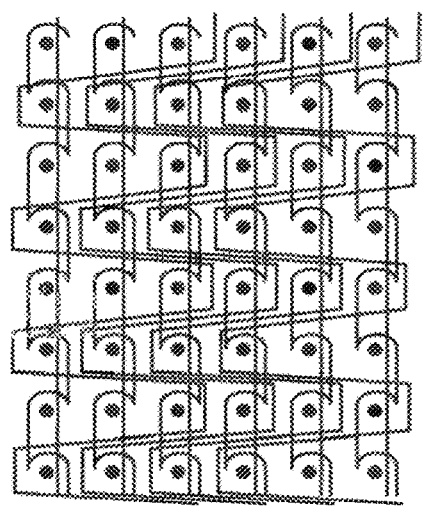
FIG. 2B is a conceptual illustration of an alternative knit pattern usable for exterior layers of the composite scaffold in accordance with the disclosure.
Figure 2C:
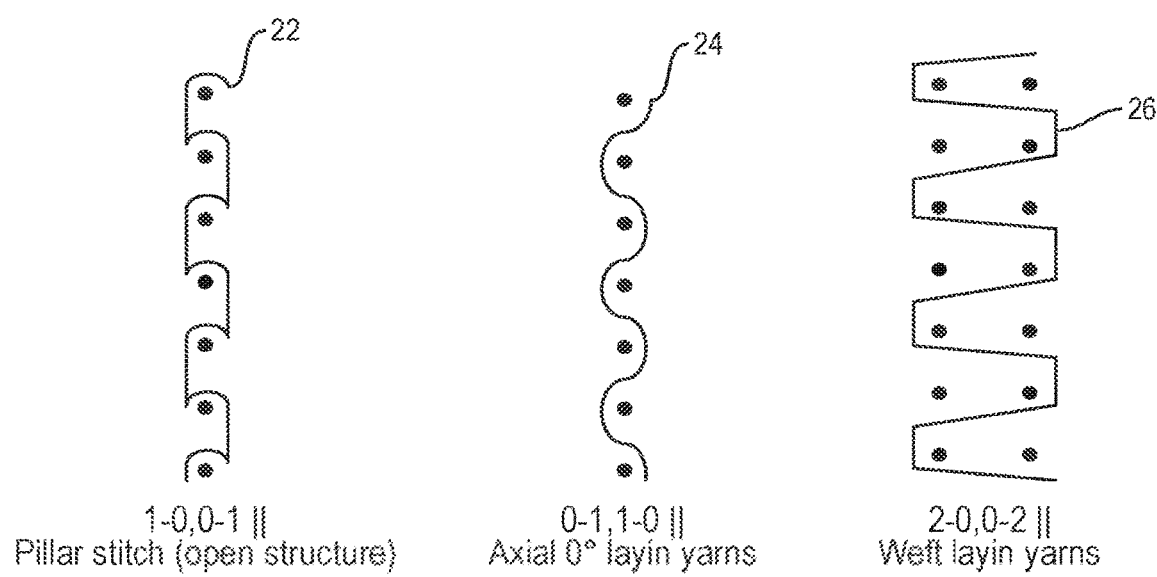
FIG. 2C is a conceptual illustration of the yarn components patterns comprising the exterior layers of FIGS. 2A-B in accordance with the disclosure.
Figure 3A:
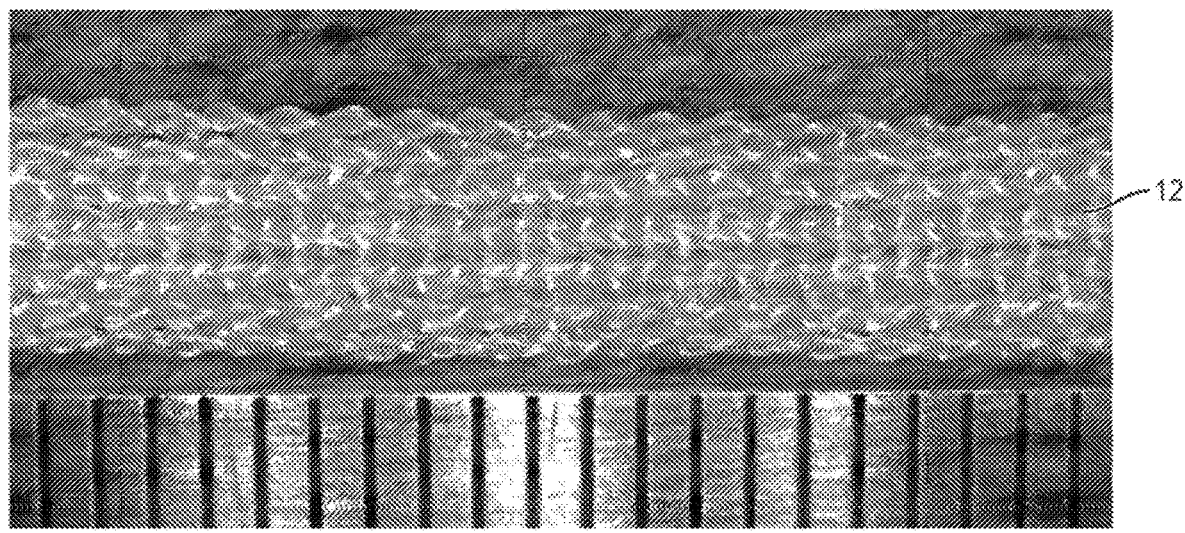
FIG. 3A is a photograph of a plan view of a composite scaffold having at least on exterior layer made in accordance with the pattern of FIG. 2A in accordance with the disclosure.

In embodiments, one or both of outer layers 12 and 14 of support structure 5 may be implemented with a warp knit open pillar stitch 22 using double yarns, as illustrated in FIGS. 2A and 2C, resulting in the textile layers illustrated in FIG. 3A. As can be seen from FIGS. 2A and 3A, the exterior layer comprises a series of wales connected by single weft lay-in 26 yarn and having double 0° straight lay-in yarns 24 on both sides inserted in the pillar structure, as illustrated in FIG. 2A. The pattern of the first outer layer 12 and second outer layer 14 may be the same or different. In embodiments, both outer layers 12 and 14 may have the same number of wales with spacer elements 18 connecting similar corresponding wales in each of layers 12 and 14. In embodiments, outer layers 12 and 14 may have different number of wales with spacer elements 18 connecting wales in each of layers 12 and 14.

As used herein, a wale is "a column of loops" lying lengthwise in the fabric. Each wale may be a single or double fiber to increase strength, but consequently increasing bulk. Increasing the number of wales, or the number of yarns per wale, will result in increasing the ultimate tensile strength of the fabric. By adjusting the number of wales, the width of the fabric can changed, which allows the same textile design to be applied to narrow applications, such as for ACL augmentation. e.g. 5 mm wide, to moderately wide applications, such as for Rotator Cuff, e.g. 23 mm wide, to very wide applications, such as for Hernia, e.g. 200 mm wide. A method of increasing ultimate tensile strength, resistance to elongation and initial stiffness can be achieved by the addition of 0° straight lay-in yarns to the technical faces of the fabric. These lay-in yarns are incorporated into each wale in a linear fashion.

A machine that has been used to manufacture the scaffold 10 is a Karl Mayer Double Needle Bar Warp Knitting Machine. These machines are computer controlled and allow modification of many parameters to effect changes to the textile properties. Key variables include the number of wales, the number of yarns per wale, addition of In-lay yarns to wales, In-lay yarn design, and number of yarns per in-lay. The ability of the fabric to stretch under tensile load can be influenced by, for example, knitting together every two wales rather than every three wales together.

Figure 3B:
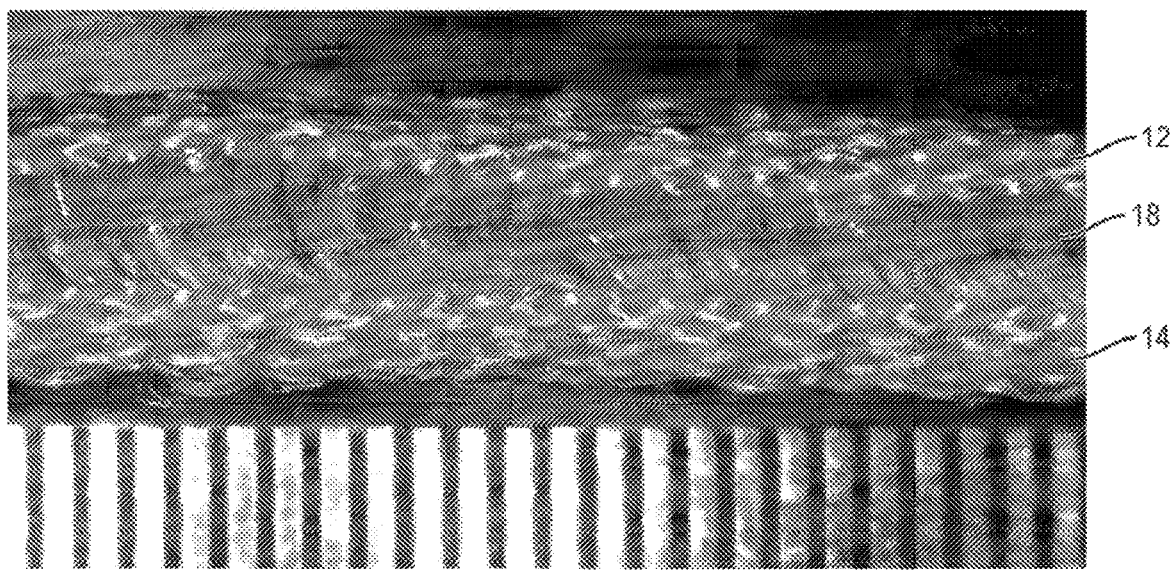
FIG. 3B is a photograph of a side view of the composite scaffold of FIG. 3A.
Figure 4A:
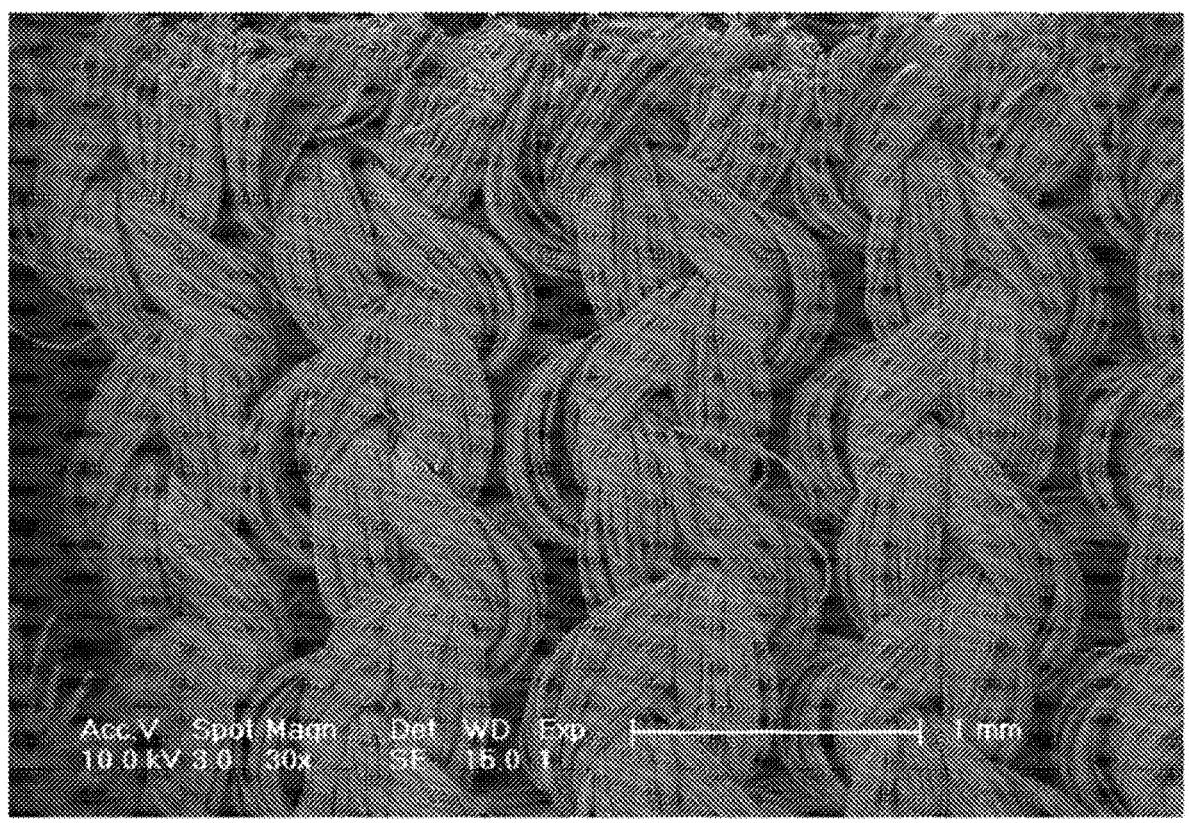
FIG. 4A is an SEM photograph of a plan view of a composite scaffold having at least on exterior layer made in accordance with the pattern of FIG. 2A in accordance with the disclosure.
Figure 4B:
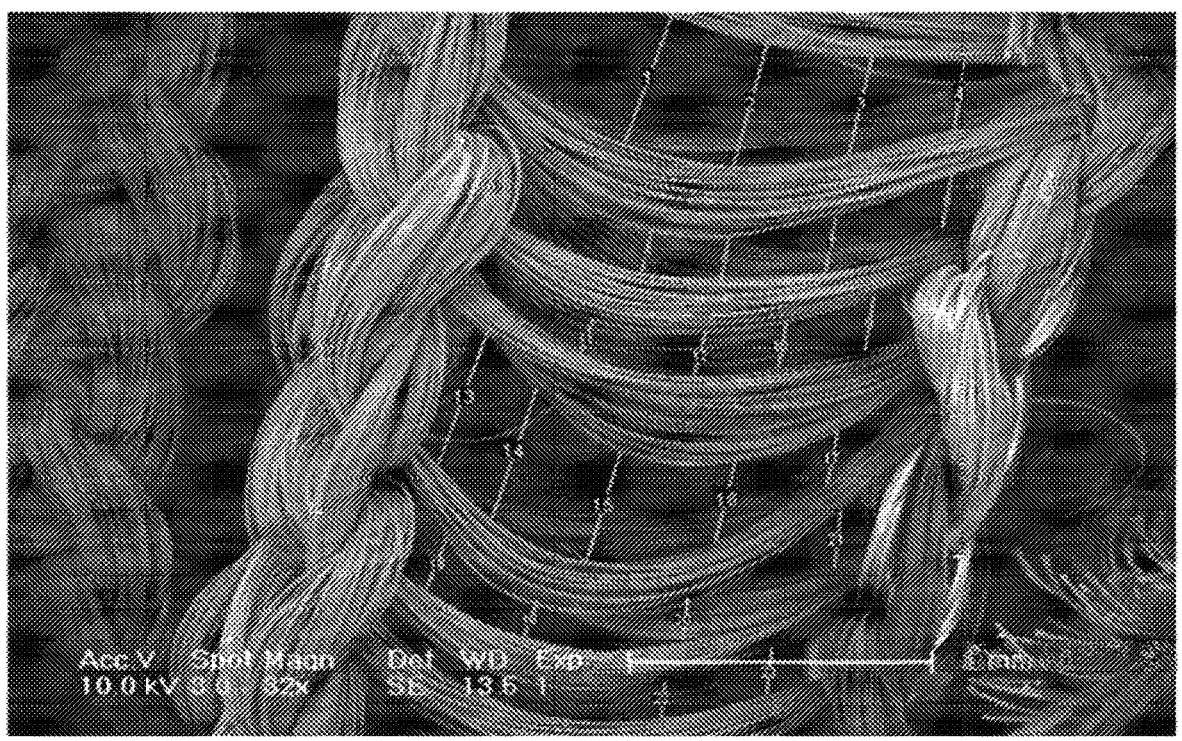
FIG. 4B is an SEM photograph of a side view of the composite scaffold of FIG. 4A.

Referring to FIGS. 3B and 4B, spacer elements 18 may be implemented with a plurality of yarns in the "Z" direction, normal to the planes in which layers 12 and 14 exist, that connect layers 12 and 14 and provide support to prevent collapse. In embodiments, each of layers 12 and 14 may have the same number of wales and spacer elements 18 may connect corresponding wales in each of layers 12 and 14. In other embodiments, spacer elements 18 may cross diagonally between different wales of layers 12 and 14. Spacer elements 18 may comprise yarns which may be monofilament, multifilament, or multifilament and/or textured.

One or both of layers 12 and 14 may be implemented using the textile pattern illustrated in FIG. 2B. Other textile patterns suitable for layers 12 and 14 may include including Full Tricot, Locknit, and Queenscord, Single Atlas, Jersey, reverse jersey, miland interlock, Milano, half Milano, etc. Variations of warp knit surface design can be utilized to adjust the dimensions, density and mechanical properties of the layers 12 and 14 including any of: surface design, number of wales, number of yarns per wale, addition of in-lay yarns to wales, in-lay yarn design, number of yarns per in-lay, lengthening or decreasing quality (machine parameter), or lengthening or decreasing gap (machine parameter).

An alternative method to warp knitting is the use of a V-Bed knitting machine, such as a Whole Garment Knitting machine, or use of a double rapier loom or a fly-shot loom to generate a woven 3D spacer fabric.

Adding pull threads between knitted panels spreads tension and keeps panels together during the manufacturing process until the pull thread is removed, without tearing or catching. These pull threads can be either mechanically removed, or dissolved away in a scour process.

In an illustrative embodiment, a support structure number five, implemented with a three-dimensional textile may have the physical parameters as illustrated in FIG. 1 below.

|  | Textile-Only |
|---|---|
| Surface Area (m2/g) | 0.2315 |
| Mass (g) | 0.0684 |
| Sample SA (m2) | 0.0158 |
| Skeletal Density (g/cc) | 1.24 |
| Skeletal Volume (cm3) | 0.0552 |
| SA:Vol (cm2:cm3) | 2871 |

A scaffold having the above physical values, and defining a void space between the first and second outer layers 12 and 14, respectively, through which plurality of spacer elements 18 extend, may be calculated to have a measurable void space surface area to volume ratio of between approximately 500 cm$^2$/cm$^3$ and 7,000 cm$^2$/cm$^3$ Subsequent to manufacture the scaffold textile may be scoured to clean it and remove any finishes that may have been used. The method of scouring can include the use of water, solvent and water solvent mixtures. The fabric may be washed constrained or unconstrained. The fabric may also be treated with an agent to modify its surface characteristics, for example, to influence its hydrophilicity. Various agents can be used for this including polyethylene glycols. The surface may also be treated to improve cell adhesion by agents such as fibrin. Where a portion of the scaffold is intended to be placed into contact with a bone region the surface of the fibers may be coated with a calcium phosphate, hydroxyapatite or bioactive glass or growth factor such as a bone morphogenetic protein, and demineralized bone matrix.

In embodiments, the composite scaffold 10, or any portion thereof, including layers 12 and 14 or spacer elements 18, may comprise any combination of synthetic bioresorbable polymers, natural polymers and/or additives. Synthetic bioresorbable polymers suitable for use as part of the composite scaffold may include, homopolymers, copolymers, or polymer blends of any of the following: polylactic acid, polyglycolic acid, polycaprolactone, polydioxanone, polyhydroxyalkanoates, polyanhydrides, poly(ortho esters), polyphosphazenes, poly (amino acids), polyalkylcyanoacrylates, poly(propylene fumarate, trimethylene carbonate, poly (glycerol sebacate), poly(glyconate), poly(ethylene glycol), poly(vinyl alcohol) and polyurethane, or any combination thereof. Natural polymers suitable for use as part of the composite scaffold may include silk, collagen, chitosan, hyaluronic acid, alginate, and an amnion-derived matrix.

Composite Scaffold Dimensions

In embodiments, the composite scaffold 10 may have a thickness, i.e. the vertical height dimension of the scaffold as opposed to the larger length and width dimensions, between approximately 0.5 mm to 5 mm, and, even more preferably between approximately 1 mm to 3 mm. Even more preferably, the scaffold may have a minimum thickness of approximately greater than or equal to 1 mm. In embodiments, the thickness of the scaffold 10 may be uniform along a length thereof or may vary in a repeating or non-repeating manner, depending on the particular application for which the scaffold will be utilized.

In embodiments, the disclosed composite scaffold 10 may have width dimensions between approximately 2 mm to 1000 mm, depending on the particular application for which the scaffold will be utilized. In embodiments, the width of the disclosed scaffold may be uniform or may vary in a repeating or non-repeating manner, depending on the particular application for which the scaffold will be utilized. For example, a scaffold 10 may have ends were in the width of the scaffold narrows and dimensionally transitions into a suture-like dimension or is modified to attach to conventional suture used in the procedures described herein.

In embodiments, the disclosed composite scaffold may have length dimensions between approximately 2 to 1000 mm, and, even more preferably greater than or equal to approximately 10 inches, again, depending on the particular application for which the scaffold will be utilized. In embodiments, the disclosed scaffolds may be manufactured in different incremental lengths or may be manufactured in lengths which may be cut or customized by practitioner as desired. FIG. 4B is an SEM photograph of a side view of the composite scaffold 10 may have length dimension and formed from a pair of outer layers 12 and 14 separated by a plurality of spacer elements 18. The photograph of FIG. 4B was taken with a Philips/FEI XL30 ESEM Scanning Electron Microscope (SEM) with a 1 mm scale legend shown on the image and distances along the axis of the length dimension between spacer yarn, indicated by reference lines 1-23. Table 1 displays each reference line and its respective distance value in micrometers as well as an average distance. As can be seen from Table 1, the average distance along the axis of the length dimension between spacer yarns is approximately is between spacer yarns is between approximately 200 μm and 300 μm.

TABLE 1

| BZ3S32 | |
|---|---|
| ROI # | Length (μm) |
| 1 | 522.471 |
| 2 | 486.002 |
| 3 | 395.111 |
| 4 | 272.278 |
| 5 | 171.236 |
| 6 | 177.801 |
| 7 | 221.409 |
| 8 | 201.073 |
| 9 | 213.168 |
| 10 | 174.469 |
| 11 | 137.669 |
| 12 | 171.932 |
| 13 | 556.535 |
| 14 | 537.49 |
| 15 | 444.187 |
| 16 | 327.109 |
| 17 | 202.071 |
| 18 | 216.961 |
| 19 | 146.15 |
| 20 | 173.058 |
| 21 | 219.813 |
| 22 | 141.249 |
| 23 | 176.63 |
| Avg | 273.2987826 |
| StDev | 141.0820741 |

Figure 4C:
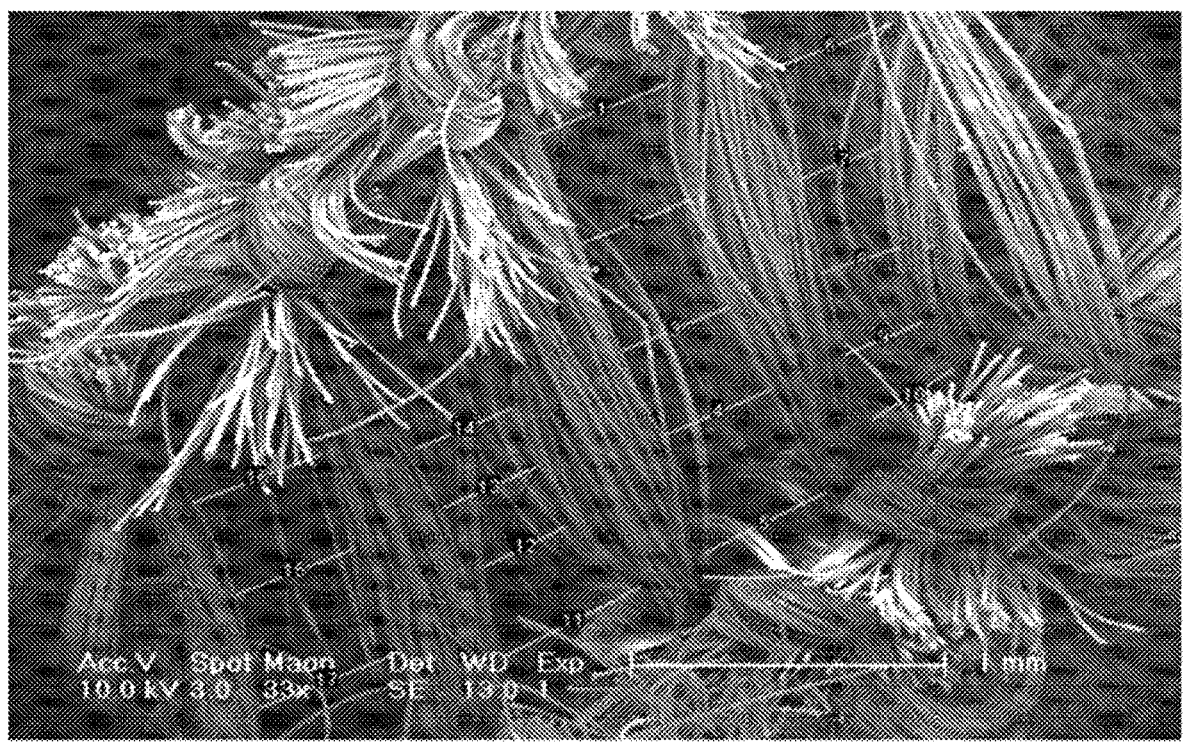
FIG. 4C is an SEM photograph of a perspective, cross-sectional view of the composite scaffold of FIG. 4A as seen along axis 4A-4A in FIG. 4A.

FIG. 4C is an SEM photograph of a perspective, cross-sectional view of the composite scaffold of FIG. 4A. The photograph of FIG. 4C was taken with a SEM with a 1 mm scale legend shown on the image and distances along a width axis, normal to the axis of the length dimension, between spacer yarns, indicated by reference lines 1-17. Table 2 displays each reference line and its respective distance value in micrometers as well as an average distance. As can be seen from Table 2, the average distance along the width axis between spacer yarns is between approximately 300 μm and 400 μm (along axis);

TABLE 2

| BZ3S32 | |
|---|---|
| ROI # | Length (μm) |
| 1 | 447.624 |
| 2 | 372.521 |
| 3 | 371.068 |
| 4 | 374.461 |
| 5 | 450.989 |
| 6 | 433.509 |
| 7 | 287.975 |
| 8 | 257.186 |
| 9 | 272.488 |
| 10 | 309.407 |
| 11 | 511.861 |
| 12 | 300.123 |
| 13 | 336.968 |
| 14 | 341.38 |
| 15 | 416.442 |

TABLE 2-continued

BZ3S32

| ROI # | Length (μm) |
|---|---|
| 16 | 444.51 |
| 17 | 477.495 |
| Avg | 376.8242 |
| StDev | 76.92161 |

In the disclosed composite scaffold 10, the respective distances between spacer elements 18, e.g. the spacer yarns, create a series of substantially parallel, similarly sized channels extending through the void between outer layers 12 and 14. These channels provide space within the interior of the support structure into which the microporous matrix 15 may be formed, as described herein. Importantly, these channels form along the axis of the device such that a contiguous channel exists between the two ends of the scaffold. Upon replacement by neo tissue, the neo tissue is substantive along the axis of the device and is hence load bearing and thus a functional tissue.

Support Structure Additives

A composite scaffold 10 made of any of the foregoing materials may be combined with additives to enhance various characteristics of the scaffold including to encourage regeneration of cell growth. Such Additives suitable for use as part of the composite scaffold may include biologics including seeded cells, biological aspirates, and bio-active agents. Seeded cells suitable for use as part of the composite scaffold may include adipose derived stem cells, mesenchymal stem cells, and induced pluripotent stem cells, or any combination thereof. Biological aspirates suitable for use as part of the composite scaffold may include whole blood, platelet rich plasma and bone marrow aspirate concentrate, or any combination thereof.

Bio-active agents suitable for use as part of the composite scaffold 10 may include growth factors, extracellular matrix molecules and peptides, therapeutics, and osteoinductive or osteoconductive agents, or any combination thereof, and may be added to the support structure 5 before formation of the microporous matrix 15 or thereafter.

Growth factors suitable for use as part of the composite scaffold may include transforming growth factor-beta superfamily (e.g. transforming growth factor-beta, bone morphogenetic proteins), insulin-derived growth factor, platelet-derived growth factor epidermal growth factor, Interleukin 1-receptor antagonist, fibroblast growth factor and vascular endothelial growth factor, or any combination thereof.

Extracellular matrix molecules and peptides suitable for use as part of the composite scaffold may include tenascin-C, hyaluronic acid, glycosaminoglycans (e.g. chondroitin sulfate, dermatan sulfate, and heparan sulfate), fibrin, thrombin, small leucine rich peptides (e.g. decorin and biglycan), fibronectin, elastin and arginine-glycine-aspartate (RGD) peptide, or any combination thereof.

Therapeutics suitable for use as part of the composite scaffold may include non-steroidal anti-inflammatories (NSAIDs) (e.g., aspirin, ibuprofen, indomethacin, nabumetone, naproxen, and diclofenac), steroidal anti-inflammatories (e.g., cortisone and hydrocortisone), antibiotics or antimicrobial agents, or any combination thereof.

Osteoinductive or osteoconductive agents suitable for use as part of the composite scaffold may include tricalcium phosphate, hydroxyapatite, and bioactive glass, or any combination thereof.

Microporous Matrix

An optional microporous matrix 15 may be formed within the interior void space 16 of composite scaffold 10. The microporous matrix 15 is supported and retained by support structure 5 and provide a support for cells to populate, proliferate. The microporous matrix 15 is resorbable or degradable and is designed to be rapidly replaced by neo tissue. A microporous matrix made from the materials described herein, on its own would not have the mechanical strength characteristics to be usable, both in terms of tensile strength and resistance to compression.

In embodiments, disclosed is a method of making a composite scaffold comprising constructing a three-dimensional support structure extending along a length dimension between first and second ends thereof and defining an interior surface within the support structure; and forming a microporous matrix within the interior surface, the microporous matrix having a multitude of interconnected pores 60 in fluid communication with exterior surfaces of the support structure. The microporous matrix is formed so that a plurality of the interconnected pores 60 are oriented relative to the dimensional characteristics of the support structure. For example, those pores closest to exterior surfaces of the composite matrix may be oriented substantially normal, or radially inward extending, relative to the closest exterior surface of the support structure. In addition, other of the plurality of interconnected pores 60 may be oriented towards the length dimension of the support structure in a manner that mimics the orientation of spacer elements 18, e.g. spacer yarns, separating the outer layers 12 and 14.

In embodiments, microporous matrix 15 may be implemented with a high surface area material such as any of a sponge, foam, or textured fibers or yarns, or any combination thereof. Methods for fabrication of the microporous matrix 15 may comprise any of lyophilization, particulate leaching, open cell extrusion, solvent casting, solid-state foaming, and cross-linking. In one embodiment, sponges/foams useful as the microporous matrix may comprise any of freeze-dried sponge, open cell extrusion foam and particulate leached sponge, or any combination thereof.

A material suitable to implement microporous 15 is collagen, including bovine type 1 collagen. Other materials that can be used for porous matrix 15, in place of or in addition to collagen, include hydrogels based on Polyethylene Glycol (PEG), Polycaprolactone (PCL), or Poly (glycolide-co-caprolactone) (PGCL), or a combination thereof. A collagen solution can be infiltrated into support structure 5 with the help of a mold to hold the scaffold. The secondary scaffold material may also coat the exterior surfaces of support structure 5 in an encapsulating manner. The mold, with textile and collagen solution, may be placed into a shelf lyophilizer, also known as a freeze dryer that uses temperature-controlled shelves to freeze the contents of the mold to a very cold temperature, e.g. down to −55 C, which creates a crystalline structure within the collagen solution causing a matrix of interconnected pores to be formed within the collagen structure occupying the interior void space 16 of support structure 5. A vacuum is pulled in the lyophilizer chamber, and the shelf temperature gradually increased, providing energy to the frozen solvent, allowing the process of sublimation to occur. The sublimated solvent is collected in a separate condenser and fully removed from the inflammation. After a period of warming and vacuum, a highly porous, low density collagen matrix is formed within the textile.

The porosity of the collagen within the microporous matrix 15 can be influenced during this process in multiple ways. Bulk porosity can be increased or decreased by decreasing or increasing the collagen solution weight percentage, respectively. The size of the pores can be adjusted by changing the rate of freezing in the mold. Increasing the rate of freezing decreases the average size, and decreasing the rate of freezing increases the average size.

Since the total surface area of the pores is related to the pore size, e.g. a large quantity of small pores will have more surface area than fewer larger pores, increasing the rate of freezing increases decreases the average pore size therefor increasing the total surface area, while decreasing the rate of freezing increases the average size therefore decreases the total surface area of the microporous matrix. FIG. 5D is a graph illustrating the relationship of temperature, pressure and time during the during the lypholization process.

Variations in mold material, including Delrin, Aluminum, Stainless Steel, or other materials, transfer heat differently and can result in different microporous matrix structures by altering crystallization in the collagen solution as it freezes. For example, a mold made of Delrin, a thermoplastic used in precision parts manufacturing, transfers heat more slowly causing larger pore sizes to form within the collagen solution. Conversely, a mold formed of aluminum transfers heat very quickly resulting in a microporous matrix with relatively small size pores. A mold made of stainless steel transfers heat more slowly than aluminum and results in larger pores than those generated with an aluminum mold, but smaller than those generated with a Delrin mold.

In addition, adjusting the thickness of the mold, between the bottom surface of the mold and the bottom of the cavity has a similar effect of increasing or decreasing heat transfer speed, which can result in different microporous matrix structures. In embodiments, or the molds shown in FIGS. 5A and 5B are made from stainless steel and have the cavity dimensions listed in table 2 below, wherein the 5×260 mm column of dimensions refers to the mold 50 illustrated in FIG. 5A and the 23×30 mm column of dimensions refers to the mold 57 illustrated in FIG. 5B. Mold 50 defines a plurality rectangular cavities 52 and has clamps 54 with pins 55 securable at the ends thereof. Mold 57 includes an array of rectangular cavities 59 and threw holes 53.

TABLE 2

|  | 5 × 260 mm | 23 × 30 mm |
| --- | --- | --- |
| Cavity Width | 5.21 | 23.20 |
| Cavity Length | 260.00 | 30.20 |
| Cavity Depth | 4.09 | 8.00 |
| Distance from bottom of cavity to bottom of mold | 4.70 | 4.70 |

The mold illustrated in FIG. 5A utilizes end clips made of Delrin, which are securable to the main mold body and which may be used to clamp the textile scaffolds during the lypholization process.

In an illustrative embodiment the cavity 52 of mold 50 have a substantially rectangular cross-sectional shape. Other cross-sectional shapes may be utilized to maximize the contact between surface area of the support structure five during the process of forming the microporous matrix therein. In particular, scaffolds having any of a D-shape, U-shape, O-shape, or C-shape may be utilized during the lypholization to maximize the surface area of the shape of the scaffold and further facilitate orientation of the pores with the microporous matrix the lypholization process. In particular, for a support structure five having a cylindrical or tubular shape, tube shaped molds, whether oriented horizontally or vertically may be utilized during the the lypholization process.

Alignment of pores relative to a dimension of the scaffold can be created via contact with the mold surfaces. As illustrated in the cross-sectional SEM photographs of FIGS. 6D-E, 6G-H, it is seen that pores within the microporous matrix 15 form, proximate the mold surface perpendicularly to the plane of contact with the mold. In embodiments, applicant has found that pores may be oriented between proximally 45° and 135° to the plane of contact with the mold. In embodiments, with a mold similar to that illustrated in FIG. 5A, a substantial number of pores will orient normal to the contact surfaces with the mold interior towards the center of the support structure 5. Such orientation further facilitates the ingrowth of cells into the composite scaffold 10 more rapidly.

An alternative mold design utilizes a similar cavity as above, but with the addition of a securely fashioned and air-tight top lid. Vacuum, or pressure, or other means may be used to fill the mold with collagen solution from one end, similar to injection molding, and release trapped gasses at another end, helping to further align the collagen fibers during the injection process.

An additional alternative mold design uses cavities that place the textile on its side, so that the faces of the textile are perpendicular to the bottom face of the mold. An additional alternative mold design may use cavities that have a "U" shaped cross-sectional profile or another shape, which will create a finished scaffold shaped more applicably for a specific type of implantation.

There are various methods to manufacture may be used to create a microporous matrix within the void space of the textile support structure, including salt leaching, gas extrusion, and other methods using either high pressure, or vacuum, and gasses.

The resorption and mechanical characteristics of the microporous matrix may be further modified by crosslinking. Generally, materials used for crosslinking have potential cyctotoxicity so being able to use lower levels is greatly beneficial. It is a benefit of the disclosed procedure that the use of the support structure 5 allows the microporous matrix 15 to utilize a low level of crosslinking. The 3D textile, infilled with a dry, highly porous and low-density collagen microporous matrix, is removed from the mold cavities and placed into a sealed chamber on a permeable shelf, such as a wire rack. A formaldehyde and ethanol solution is poured into a tray, and this tray is placed under the rack of scaffold, and the chamber door sealed. The tray fully encompasses the base dimensions of the chamber (L×W) and the vapor from the solution is used to crosslink the collagen within the 3D textile. After a set time, the tray is removed, and the product is moved into an aeration chamber, in which clean, dry air, or alternatively, another gas such as Nitrogen, is pumped through and out of the chamber, which effectively stops the crosslinking process. Crosslinking of the collagen can be increased by increasing the time in the chamber, increasing concentration of formaldehyde in the ethanol solution, or reducing the aeration. Likewise, crosslinking can be decreased by decreasing time in the chamber, decreasing concentration of formaldehyde in the ethanol solution.

Alternatively a chemical cross linking agent may be added to the collagen solution. These agents may include, but are not limited to, various concentrations of aldehydes such as glutaraldehyde, genipin, 1-ethyl-3-(3-dimethylaminoipropyl) carbodiimide (EDC), and EDC/N-hydroxysuccinimide (EDC/NHS). An additional alternative mode of crosslinking may come in the form of photochemically activated crosslinking, which may involve the use of UV or visible light to trigger a crosslinking process with or without a crosslinking initiator.

Composite Scaffold Mechanical Characteristics

The mechanical characteristics of the composite scaffolds 10 disclosed herein, result in a composite scaffold optimized for use in a wide array of medical procedures including to reinforce a suture repair, stand alone repair or reconstruction, or reconstruction using a tissue graft and for fixation purposes. Composite scaffolds 10 made in accordance with the description herein as well as Examples 1, 2 and 3 were tensile tested using a Mark-10 Tensile Tester with a crosshead speed of 20 mm/min, with the results listed in Table 3.

TABLE 3

| | | | | | Textile | | | | |
|---|---|---|---|---|---|---|---|---|---|
| Force (N) | Displacement (mm) | % Extension | Width (mm) | Thickness (mm) | Cross Sectional Area (mm$^2$) | Change Width % | Change Thickness % | Change Cross Section Area % | Change volume in % |
| 0 | 0 | 0% | 4.81 | 3.14 | 15.1 | | | | |
| 1 | 1 | 3% | 4.79 | 3.02 | 14.47 | −0.4% | −3.8% | −4.2% | −2% |
| 4.5 | 2 | 5% | 4.79 | 2.83 | 13.56 | −0.4% | −9.9% | −10.2% | −6% |
| 11.5 | 3 | 8% | 4.64 | 2.48 | 11.51 | −3.5% | −21.0% | −23.8% | −18% |
| 22 | 4 | 10% | 4.64 | 2.18 | 10.12 | −3.5% | −30.6% | −33.0% | −26% |
| 35 | 5 | 13% | 4.57 | 2.17 | 9.92 | −5.0% | −30.9% | −34.3% | −26% |
| 46.5 | 6 | 15% | 4.48 | 2.02 | 9.05 | −6.9% | −35.7% | −40.1% | −31% |
| 55 | 7 | 18% | 4.44 | 2.02 | 8.97 | −7.7% | −35.7% | −40.6% | −30% |
| 61.5 | 8 | 20% | 4.38 | 1.91 | 8.37 | −8.9% | −39.2% | −44.6% | −34% |
| 68 | 9 | 23% | 4.38 | 1.86 | 8.15 | −8.9% | −40.8% | −46.0% | −34% |
| 74.5 | 10 | 25% | 4.35 | 1.81 | 7.87 | −9.6% | −42.4% | −47.9% | −35% |
| 81 | 11 | 28% | 4.25 | 1.79 | 7.61 | −11.6% | −43.0% | −49.6% | −36% |
| 88 | 12 | 30% | 4.27 | 1.73 | 7.39 | −11.2% | −44.9% | −51.1% | −36% |
| 94 | 13 | 33% | 4.21 | 1.71 | 7.2 | −12.5% | −45.5% | −52.3% | −37% |
| 101 | 14 | 35% | 4.18 | 1.64 | 6.86 | −13.1% | −47.8% | −54.6% | −39% |
| 108.5 | 15 | 38% | 4.15 | 1.6 | 6.64 | −13.7% | −49.0% | −56.0% | −40% |
| 116 | 16 | 40% | 4.12 | 1.54 | 6.34 | −14.3% | −51.0% | −58.0% | −41% |
| 124 | 17 | 43% | 4.09 | 1.52 | 6.22 | −15.0% | −51.6% | −58.8% | −41% |
| 131 | 18 | 45% | 4.05 | 1.52 | 6.16 | −15.8% | −51.6% | −59.2% | −41% |
| 136.5 | 19 | 48% | 3.98 | 1.48 | 5.89 | −17.3% | −52.9% | −61.0% | −42% |
| | 20 | 50% | 3.96 | 1.48 | 5.86 | −17.7% | −52.9% | −61.2% | −42% |

An advantage of the composite scaffold 10, and particularly, the support structure 5, as disclosed herein, is its ability to resist compression upon elongation. In embodiments, as can be seen from the values in Table 3 above, the width, height and cross-sectional area of the three-dimensional textile comprising support structure 5 resists compression upon substantial forces. In particular, for a support structure 5 having a cross-sectional area of approximately 9.92 mm$^2$, a thickness (height) of approximately 2.17 mm and a width of approximately 4.57 mm, extension of the support structure 5 along its length axis by force of 35 N causes an approximately 13% extension of the length dimension of the support structure 5. In embodiments, the thickness dimension of the support structure changes less than approximately 31% upon elongation of the length dimension by approximately 13%. In embodiments, the cross-sectional area changes less the approximately 35% upon elongation of the length dimension by approximately 13%. In embodiments, the width dimension of the support structure changes less than approximately 5% upon elongation of the length dimension by approximately 13%.

In embodiments, a length of a support structure 5, implemented with a three-dimensional textile scaffold as disclosed herein, may have an ultimate load at a percentage of elongation of the length dimension between approximately 30% and 125%. In embodiments, the scaffold may have a yield at a percentage of elongation of the length dimension between approximately 5% and 15%. In embodiments, the scaffold may have a tenacity of between approximately 0.073 grams-force/denier and 1.102 grams-force/denier. In embodiments, the scaffold may have a stiffness of approximately between 2.5 N/mm and 25 N/mm, wherein the stiffness defines an extent to which the scaffold resists deformation in response to an applied force. In embodiments, the scaffold may have a strain at failure of approximately between 20% and 70%. In embodiments, the scaffold may have a tenacity at failure approximately between 0.3 grams-force/denier and 2 grams-force/denier.

In an illustrative embodiment, the support structure 5, implemented with a three-dimensional textile scaffold 5 mm in width and 40 mm in length and having a thickness approximately 1 mm, or as disclosed herein, may have an ultimate load displacement of approximately between 5 mm and 50 mm, wherein the ultimate load displacement defines a change in displacement at an amount of load applied to the biomimetic scaffold beyond which the biomimetic scaffold will fail. Such test being done with a 40 mm gauge length and in accordance with the standards set forth by the American Society for Testing and Materials (ASTM). In the illustrated embodiment, the scaffold may have a yield displacement of approximately between 1 mm and 8 mm, wherein the yield displacement defines a change in displacement at which the biomimetic scaffold begins to deform. In the illustrated embodiment, the scaffold may have a yield force of approximately between approximately 20 N and 70 N, wherein the yield force defines a force at which the biomimetic scaffold begins to deform. In the illustrated embodiment, the scaffold may have a stiffness of approximately between 2.5 N/mm and 25 N/mm, wherein the stiffness defines an extent to which the biomimetic scaffold resists deformation in response to an applied force. In the illustrative embodiment, the scaffold may have an ultimate strain of approximately between 20% and 70%, wherein the ultimate strain defines the deformation of the biomimetic scaffold due to stress. In the illustrated embodiment, the scaffold may have an ultimate load approximately between 100 N and 200 N wherein the ultimate load is defined as the amount of load applied to the biomimetic scaffold beyond which amount the scaffold fails. In the illustrative embodiment, the scaffold may have an ultimate strength approximately between 2.5 MPa and 20 MPa wherein the ultimate strength is defined as a capacity of the biomimetic scaffold to withstand loads tending to elongate the biomimetic scaffold. In the illustrative embodiment, the scaffold may have an ultimate stress approximately between 2.5 MPa and 20 MPa wherein the ultimate stress is defined as a maximum value of stress that the structure can resist beyond which maximum value the structure fails. In the illustrated embodiment, the scaffold may have a modulus of approximately between 2.5 MPa and 70 MPa, wherein the modulus defines measure of stiffness of the biomimetic scaffold with the void space. In illustrative embodiment, the scaffold may have a modulus of approximately between 150 MPa and 600 MPa, wherein the modulus defines measure of stiffness of the biomimetic scaffold without the void space, where the modulus is calculated using a cross-sectional area of only material comprising the composite scaffold.

According to embodiments, the composite scaffold disclosed herein provides greater support for a larger quantity of regenerated tissue through staggered degradation rates of the scaffold components. More specifically, the first and second support matrixes 5 and 15 of scaffold 10 have different degradation rates. In one embodiment, the second support matrix 15, e.g. the sponge, degrades 2 to 12 times faster than the first support structure 5 based on mass loss or molecular weight loss. For example, the sponge comprising the second support matrix may have a mass loss by 3 to 6 months following implementation whereas the textile weave comprising first support matrix may have mass loss at 12 months following implantation. Such difference in the rate of degradation enables the considerable tissue ingrowth facilitated by the interior void of the scaffold 10 to continue to be supported by the textile fabric for a longer period of time. As indicated, the parameter of material degradation may be measured via loss of mass or molecular weight loss. In one embodiment, the composite scaffold may have a degradation profile of greater than or equal to 50% strength retention for at least approximately four weeks after implantation and a mass loss of 100% mass loss between approximately six and twelve months after implantation.

According to embodiments, the composite scaffold disclosed herein may have features which enhance usability and better performance once implanted. In embodiments, the scaffold 10 may have ends that narrow and transition into suture-like dimensions or are modified, e.g. stitched or knotted, to attach to conventional suture used in the procedures described herein. In embodiments, the support structure 5, e.g., the textile, has ends or edges that are modified to be heat set or embroidered or impregnated with other materials to facilitate better handling, better integration with the existing tissue and to further reduce dimensional distortion of the scaffold 10 under pressure, tensile, or shear forces. In embodiments selected sections of the scaffold 10 may be repeated, either randomly or with fixed rapidity to increase or decrease the density of the scaffold by increasing or decreasing the density of the textile, for example, by a change in the textile pattern of the first support structure 5. In embodiments, such repeat regions may be chosen to alter the surface finish of the scaffold by altering the parameters of lyophilization, smoothness or roughness, of the exterior surface of the scaffold to enhance acceptance of the scaffold once implanted.

Figure 2D:
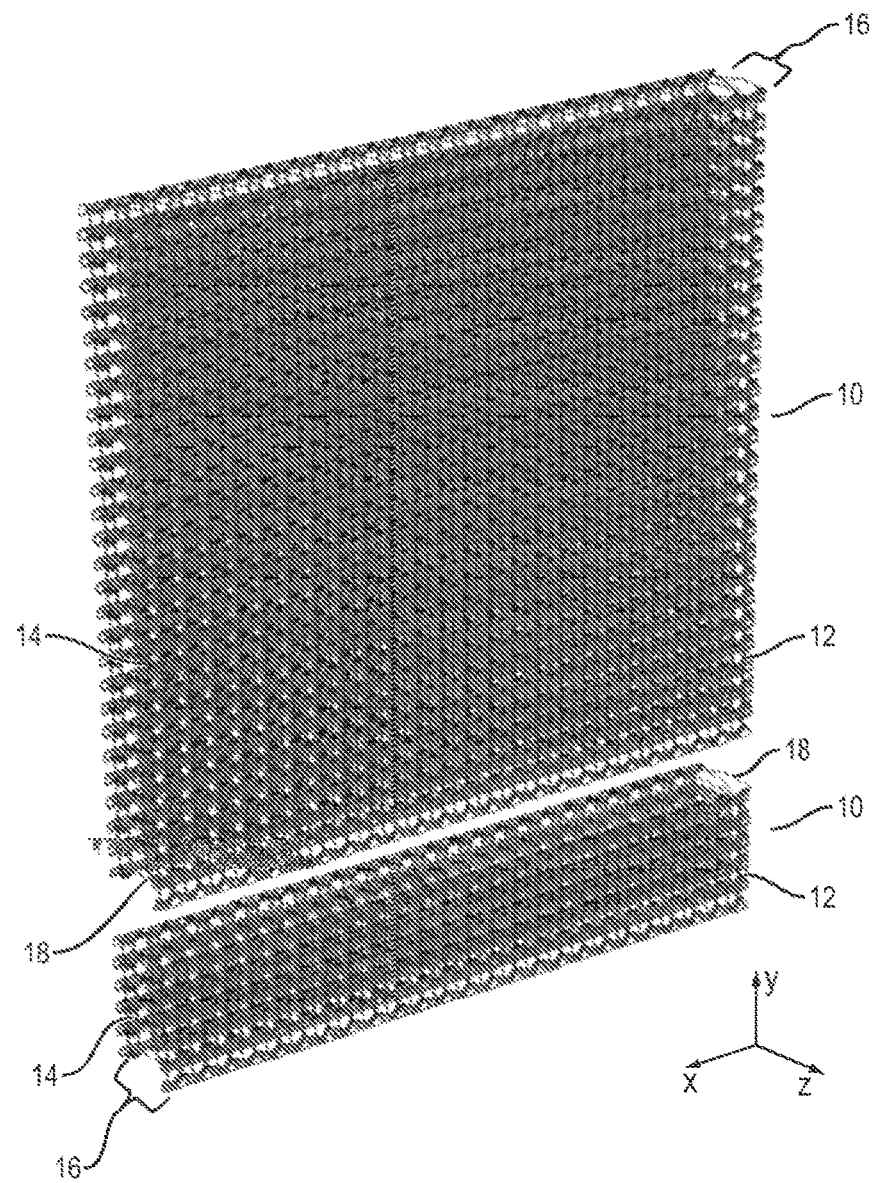
FIG. 2D is a conceptual illustration of a perspective view of textile patterns for a pair of composite scaffolds useful for ACL and rotor cuff procedures in accordance with the disclosure.

In embodiments, the spacer elements 18 may be located in only part of the interior space 16 of scaffold 10, e.g. a hollow lumen, as illustrated in FIG. 2D. In other embodiments, the spacer elements 18 may have any of a regular or irregular repeating placement pattern within the interior space 16 between the layers 12 and 14 of the scaffold 10. In other embodiments, the spacer elements 18 themselves may be implemented with a textile, such as felt, or tissue or tissue derived materials, or as otherwise described herein.

According to embodiments, the composite scaffold could also be seeded with cells for a temporary pre-culture period to allow the cells to elaborate a collagen-rich extracellular matrix on the sponge and textile components. The scaffold could then optionally be decellularized to leave a matrix template having native extracellular matrix proteins on the textile structure and the scaffold subsequently implanted to repair a tendon or ligament in vivo.

Scaffold Pore Characteristics

Multiple samples of composite scaffolds manufactured in accordance with examples one and two and the processes described herein were tested to determine various behavioral characteristics as described below. The microporous matrix in each sample composite scaffold has a multitude of interconnected pores opening to an exterior surface of the microporous matrix and the composite scaffold. Various characteristics of the pores within the microporous matrix, and, accordingly, the composite scaffold, are measurable by Mercury Intrusion Porosimtery (MIP) or gas adsorption. Mercury is a non-wetting liquid that will not actively infill into porous structures. However, by applying pressure, using MIP, mercury can be forced into the pores of the microporous matrix, with higher pressures allowing the mercury to enter smaller pores. By accurately monitoring a volume of mercury while step-wise increasing the applied pressure, pore size (diameter) and pore volume can be accurately measured. The pore size and volume measurements can be used to determine multiple properties of the microporous matrix and the composite scaffold generally.

Surface Area

An important characteristic of the disclosed composite scaffolds is the ratio of the scaffold surface area per unit weight of the scaffold. The disclosed composite scaffold, due to the extensive multitude of interconnected pores within the microporous matrix supported by the 3D textile support structure, has a large surface area onto which cell migration and subsequent neo-tissue development may occur. The total surface area of the interconnected pores and the exterior of the composite scaffold is more accurately measurable using MIP, instead of just geometric dimensions and image quantification. Surface area may be calculated from the known diameter of the pores, measured via MIP, by assuming the pores are spheres using the following formula:

$$A=4\pi r^2$$

As such, the surface area parameter represents an amount of surface area of the composite scaffold per unit weight of the composite scaffold area, measurable in meters squared per gram (m²/g). FIG. 8 is a graph 80 of test data showing the relationship of the cumulative total pore surface area relative to pore diameter, measured in micrometers, for a number of composite scaffold samples as well as a sample comprising only the 3D textile comprising support structure 5. In the samples of FIG. 8, the 3D textile support structure 5, whether alone or populated with a microporous matrix 15, comprised PLLA fibers. All samples were produced in accordance with the methods and Examples 1 and 2 described herein. In embodiments, a disclosed composite scaffolds may have a surface area per weight unit which range from between approximately 0.3 m²/gram and 1.5 m²/gram. The disclosed composite scaffolds may have a surface area per weight unit which range from between approximately 0.6 m²/gram and 1.2 m²/gram. The disclosed composite scaffolds may have a surface area per weight unit, from between approximately 0.71 m²/gram and 1.0 m²/gram.

The total surface area of the interconnected pores and the exterior of the composite scaffold is also more accurately measurable using gas adsorption, instead of just geometric dimensions and image quantification, such as with krypton gas. The Table below illustrates two samples having a 5 mm width and a 40 mm length. The surface area of the composite scaffold is between approximately 0.3 m²/gram and 15 m²/gram, as measured by krypton gas adsorption for pores having a diameter less than 1 µm.

| Sample | BET SA (m2/g) |
| --- | --- |
| 5 mm | 0.5826 |
| 5 mm | 0.5558 |

Total Pore Volume

Another important characteristic of the composite scaffold is the high volume of void space due, in part, to the number, size, orientation and interconnectivity of the pores which collectively define void space within the microporous matrix. Such high total pore volume facilitates more rapid blood absorption, cell migration and subsequent neo-tissue development. The total volume of pores collectively forming the void space within the microporous matrix may be measured directly using MIP by monitoring the change in Mercury volume during the MIP process. As such, the pore volume parameter of the composite scaffold represents a total cumulative void volume per unit weight of the composite scaffold, e.g. cm³/g. FIG. 9 is a graph 90 showing the relationship of the cumulative total pore volume as measurable in centimeters cubed per gram relative to pore diameter, as measured in micrometers for a number of composite scaffold samples as well as only the textile only support structure. In the samples of FIG. 9, the textile support structure, whether alone or populated with a microporous matrix, comprises PLLA fibers. All samples were produced in accordance with the methods described herein. In embodiments, the disclosed composite scaffold may have a total pore volume which ranges from between approximately 3.0 cm³/gram and 9.0 cm³/gram. The disclosed composite scaffolds may have a volume which ranges from between approximately 3.5 cm³/gram and 7.0 cm³/gram. The disclosed composite scaffolds may have a total pore volume which ranges from between approximately 4.0 cm³/gram and 5.0 cm³/gram.

Porosity

Another important characteristic of the composite scaffold is porosity, that is the measurement of the void space volume within the microporous matrix as a percentage of the measurable volume of the composite scaffold itself. Such calculation may be done using measurements taken during MIP. During the MIP process, the mass of each sample is known, as is the occupied volume of the sample by monitoring mercury volume. At the lowest applied pressure during MIP, there should be no mercury infill into the scaffold, so bulk density of the composite scaffold can be calculated. At the higher applied pressures during MIP, the composite scaffold should be near-complete mercury infill. Accordingly, the scaffold skeletal density can be calculated as follows:

Porosity=100*1–(density at low pressure/density at high pressure)

In this manner, the measurable volume of the composite scaffold is not calculated geometrically but through relative densities. FIG. 10 is a graph 100 of the relationship of the composite scaffold density in grams per cubic centimeter in relation to Mercury pressure, as measured in pounds per square inch absolute, i.e. in a vacuum, measured in micrometers, for a number of composite scaffold samples as well as only the textile only support structure. In the samples of FIG. 10, the textile support structure, whether alone or populated with a microporous matrix, comprises PLLA fibers. All samples were produced in accordance with the methods described herein. In embodiments, the disclosed composite scaffold may have a porosity which ranges from between approximately 75% to 98%. In embodiments, the disclosed composite scaffold may have a porosity which ranges from between approximately 80% to 90%. In embodiments, the disclosed composite scaffold may have a porosity which ranges from between approximately 80% to 85%.

Permeability

Another important characteristic of the composite scaffold is the permeability of the microporous matrix which facilitates more rapid absorption of fluids, particularly blood, both during and after implantation, to accelerate the process of cell migration and subsequent neo-tissue development. The microporous structure, e.g. collagen, inside the textile support structure facilitates a more uniform and well-defined pore structure compared to a collagen sponge alone, with a permeability of approximately 200% of the permeability of a collagen sponge by itself. This is due, at least in part, to the more uniform and well-defined structure of interconnected pores. Reproducible permeability values can be calculated from Mercury Intrusion Porosimetry (MIP) data using the Katz-Thompson equation set forth below:

$$k = \frac{1}{89}(D_{max})^2 * \frac{D_{max}}{D_c} * \varphi * S(D_{max})$$

Where:

k (mD): air permeability

Pt (psia): pressure at which Hg starts to flow through pores $D_c$ (μm): diameter corresponding to Pt ($D_c$=180/Pt)

$D_{max}$ (μm): diameter at which hydraulic conductance is a maximum hydraulic conductance: measure of the ease that a fluid flows through a porous material φ: porosity from MIP data (subtract inaccessible void space in fibers)

$S(D_{max})$: fraction of connected pore space that is size $D_{max}$ and larger/fraction of total porosity filled at $D_{max}$ An explanation of how to calculate permeability using the above Katz-Thompson equation is set forth in a publication by Goa and Hu, entitled *estimating permeability using median poor-throat radius obtained from Mercury intrusion precocity*, J. Geophysics. Eng. (2013). In this manner, reproducible permeability values can be calculated from data collected during MIP. In embodiments, the disclosed composite scaffold may have a permeability which ranges from between approximately 1200 and 3000 millidarcy. In embodiments, the disclosed composite scaffold may have a porosity which ranges from between approximately from between approximately 1400 and 2600 millidarcy. In embodiments, the disclosed composite scaffold may have a porosity which ranges from between approximately from between approximately 1600 and 2000 millidarcy.

Total Surface Area/Scaffold Volume

Another important characteristic of the composite scaffold is the ratio of the total surface area/scaffold volume. The surface area per given sample is determinable from MIP. The skeletal density can be calculated as explained above with reference to the porosity parameter. Surface area is reported in units of square meters per sample weight unit ($m^2/g$) and can be converted to meters cubed by multiplying by the sample mass. Scaffold volume is equal to the sample mass divided by the skeletal density. In embodiments, the disclosed composite scaffold may have a void space surface area to scaffold volume between approximately 5,000 $cm^2$/$cm^3$ and 16,000 $cm^2/cm^3$. In embodiments, the disclosed composite scaffold may have a void space surface area to scaffold volume between approximately 7,000 $cm^2/cm^3$ and 14,000 $cm^2/cm^3$. In embodiments, the disclosed composite scaffold may have a void space surface area to scaffold volume between approximately 9,000 $cm^2/cm^3$ and 12,000 $cm^2/cm^3$.

Pore Size

Another important characteristic of the composite scaffold is median pore size of the interconnected pores within the void space of the microporous matrix 15, as measured in micrometers. The pores with the microporous matrix must be large enough to allow cell infiltration while not being so large that it slows cell proliferation and formation of neotissue prior to reabsorption of the microporous matrix following implantation. In accordance with the disclosure, a number of pores of a given diameter are effectively measured by tracking intrusion volume at a given pressure during MIP. From this, median pore size and pore size distribution are both reported. FIG. 12 is a graph 120 illustrating graphically the relationship of the distribution of pore diameter, as measured in micrometers relative to the logarithmic differential volume as measured in cubic centimeters per grams. In embodiments, the microporous matrix may have a plurality of interconnected pores having a median pore size of between approximately 10 μm to 70 μm.

In embodiments, the microporous matrix may have a plurality of interconnected pores having a median pore size of between approximately 12 μm to 50 μm. In embodiments, the microporous matrix may have a plurality of interconnected pores having a median pore size of between approximately 20 μm to 35 μm.

Another important characteristic of the composite scaffold is distribution of pore sizes within the void space of the microporous matrix of the composite scaffold, as measured in micrometers. Cumulative pore volume is determinable from MIP. The fractional contribution of pores over a certain size to the void space can be calculated as cumulative void space at a given pore size divided by total void space. The distribution of pore sizes within the void space of the microporous matrix is also illustrated in FIG. 12. As can be seen from FIG. 12, the majority of the collective void space within a microporous matrix comprises pores having a size parameter greater than 10 μm. In embodiments, the microporous matrix has a multitude of interconnected pores collectively defining void space wherein at least approximately 99% of the void space comprises pores having a size dimension of 10 μm or greater. In embodiments, the microporous matrix has a multitude of interconnected pores collectively defining void space wherein at least approximately 95% of the void space comprises pores having a size dimension of 10 μm or greater. In embodiments, the microporous matrix has a multitude of interconnected pores collectively defining void space wherein at least approximately 80% of the void space comprises pores having a size dimension of 10 μm or greater.

Swelling and Absorbance

According to embodiments, the composite scaffold disclosed herein provides a measurably high absorptive capacity, e.g. capable of absorbing aqueous mediums, or wickability, to facilitate more rapid and greater quantity of absorbed biologic fluids and/or cells within the scaffold. In particular, the absorbance capacity of the composite scaffold can be measured from the following formula:

% Absorbance=(Sample wet mass−samples dry mass)/Sample dry mass*100

In embodiments, the disclosed composite scaffold has a measurable dry weight value representing a weight of the scaffold in a substantially dry state and a measurable dry volume value representing a volume of the scaffold in a substantially dry state, with an increase of between approximately 200% and 600% of the weight value of the scaffold from fluid absorption changing the dry volume value of the scaffold between approximately 0% and 10%. The percent volume change of the composite scaffold can be measured from the following formula:

% Volume Change=(Sample wet volume−sample dry volume)/Sample dry volume*100

According to embodiments, the composite scaffold disclosed herein provides a reduced swelling profile, e.g. resists dimensional changes with increased absorption fluids. In particular, the percent swelling change of the composite scaffold can be measured from the following formula:

% Swell=(Sample wet mass−samples dry mass)/ (Sample wet mass)*100

In embodiments, the disclosed composite scaffold has a measurable dry weight value representing a weight of the composite scaffold in a substantially dry state and a measurable dry length value representing a dimensional parameter of the composite scaffold in a substantially dry state, with an increase of between approximately 200% and 600% of the weight value of the composite scaffold from fluid absorption changing the dry length value of the composite scaffold by less than between approximately 0% and 3%. The percent length change of the composite scaffold can be measured from the following formula:

% Length Change=(Sample wet length−sample dry length)/Sample dry length*100

In embodiments, the disclosed composite scaffold a measurable dry weight value representing a weight of the composite scaffold in a substantially dry state and a measurable cross sectional profile value representing a dimensional parameter of the composite scaffold in a substantially dry state, with an increase of between approximately 200% and 600% of the weight value of the composite scaffold from fluid absorption changing the cross sectional profile value of the composite scaffold by between approximately 0% and 10%. The percent cross sectional profile change of the composite scaffold can be measured from the following formula:

% Cross sectional profile change=((Sample wet width*sample wet height)−(Sample dry width*sample dry height))/(Sample dry width*sample dry height)*100

Other relevant form are as followsulas:

% Density Wet=((Sample wet weight/sample wet volume)/(sample dry weight/sample dry volume)*100%

% Thickness Change=(sample wet height−sample dry height)/sample dry height*100

% Weight Wet=sample wet weight/sample dry weight*100

% of Sample Volume filled=(Sample wet mass−samples dry mass)/(Sample dry volume)

Composite scaffold devices are weighed throughout the manufacturing process, capturing both the mass of the textile alone, the mass after being coated with PEG 400, and the mass after adding collagen solution and subsequent lyophilization. The mass of the collagen microporous matrix in each device can be calculated as follows:

$mass_{Collagen} = mass_{Scaffold} - mass_{textile+PEG\ 400}$

The % dry weight of the collagen compared to the whole composite scaffold device can then be calculated:

$$\% \text{ dry weight of collagen in } BioBrace = \frac{mass_{Collagen}}{mass_{Scaffold}}$$

Category Scaffold Density

Another important characteristic of the composite scaffold is scaffold density. According to embodiments, for the composite scaffold disclosed herein has a higher density or mass of the support matrix provides the primary and bulk structure of the disclosed scaffold, in comparison to the more porous matrix disposed therein. More specifically, the first and second support matrixes 5 and 15 of scaffold 10 have different densities or mass components relative to each other. In one embodiment, the first support structure 5, e.g., the textile, has a measurable mass or density which is greater than or equal to one times that of the mass or density of the second support matrix 15, e.g. the sponge, and, more preferably, between 2 to 5 times that of the mass or density of the second support matrix 15. In embodiments, the disclosed composite scaffold may have a maximum scaffold density of less than 0.5 g/cm$^3$, and specifically between approximately 0.05 g/cm$^3$ and 0.3 g/cm$^3$ Methods of Manufacture Methods for manufacturing the composite scaffold in accordance with the disclosure are as follows. A 5 mm wide, 3 mm tall, and 260 mm long composite scaffold for ACL repair or augmentation made from a three-dimensional PLLA textile filled with a highly porous collagen matrix is manufactured, as follows. A three-dimensional (3D) textile which comprises the support structure is manufactured using the double pillar pattern illustrated in FIG. 2A in accordance with the technique the warp knitting technique described. The resulting structure has top and bottom layers of 6 wales each. The corresponding wales top and bottom layers of the interconnected by a series of knitted spacing yarns extending through the void space in the Z-direction, e.g. normal to the X-Y plane of the outer layers 12 and 14, and interconnecting the layers 12 and 14. The 3D textile is received as a continuous length textile, 5 mm wide and 3 mm tall and is ultrasonically scoured, e.g. washed, in solution of DI and IPA to remove particulate and yarn spin finish. Multiple washes, replacing solution in between washes, are used. The temperature of the wash solution may be room temperature, or up to 40C. The 3D textile is then air dried, and cut to length.

An alternative method of preparing the 3-D textile prior to coating with a hydrophilic solution involves wrapping the continuous length textile, not overlapping, around a frame, also known as a tenter frame, or suture rack, with moderate tension. The wrapped frame is then submerged in a distilled water and isopropyl alcohol solution, and washed either ultrasonically or in a shaker bath for agitation. Multiple washes, replacing solution between washes, may be used. The temperature of the wash solution may be room temperature, or up to 40C. The 3D textile is then air dried on the rack, under tension. The textile is then cut to length, while under tension, on the rack, creating uniform lengths. By utilizing the suture rack, washing under tension, and drying under tension, the textile is heat-set, reducing wrinkles, keeping top and bottom textile faces opposed, and tightening the knit structure, resulting in less elongation of the final textile under load.

The scoured and cut to length of 3D textile is then submerged in a solution of polyethylene glycol (PEG) and ethanol to increase hydrophilicity. The concentration of PEG in ethanol is specifically controlled to result in a controlled weight percentage of PEG on the 3D textile. The 3D textile is then air dried. An alternative method of preparing the 3-D textile prior to coating with a hydrophilic solution involves submerging the 3D textile in the PEG and Ethanol solution, after scouring, but before cutting to length. An additional alternative method involves submerging the 3D textile as wrapped on the frame, after scouring, but before cutting, in the PEG and ethanol solution. In the above-mentioned steps, multiple combinations of each alternative may be utilized to achieve the same outcome.

Next, a 0.6% collagen solution by weight is made up using low molarity acetic acid and powder-form Type-1 bovine collagen is blended and vacuum processed to remove trapped air bubbles. A different low molarity acid such as hydrochloric acid may be used to make the collagen solution. Additionally, an alternative process may remove trapped air bubbles, for example, by spinning the solution in a centrifuge.

Different weight percent collagen solutions can be used. Increasing the weight percentage of collagen increases the amount of collagen in the matrix. Decreasing the weight percentage of collagen reduces the amount of collagen in the matrix. These changes will affect the final collagen matrix density, structural characteristics, and porosity when utilized with the lyophilization process described herein.

The stainless-steel mold 57 shown in FIG. 5B is used to guide infill of collagen solution into the 3D textile and through the next step, lyophilization, to create the collagen sponge matrix structure. The cavities of the mold are filled with a small amount of collagen solution. Then, 3D textile lengths are placed into the mold, 3D textile faces parallel to the bottom of the cavity, and clamps are used on each end to secure the 3D textiles and to prevent movement. These clamps have an additive benefit, in the following step, Lyophilization, by creating areas on each end that are flat without porous collagen matrix, used for product handling and suture attachment.

Then, additional collagen solution is filled into the cavities with the textile, completely submerging the textile in collagen solution. Then, the mold with textile and collagen solution is vacuum processed to remove remaining air within the 3D textile to completely infill the textile with solution. The mold, with textile and collagen solution, are placed into a shelf lyophilizer, and the temperature brought down to −55 C over a period of approximately 2 hrs. The textile, infilled with a dry, highly porous and low-density collagen matrix, is removed from the mold cavities and placed into a sealed chamber on a wire rack. A formaldehyde and ethanol solution is poured into a tray, and the tray placed under the rack of product, and the chamber door sealed. Vapor from the solution crosslinks the collagen within the textile. After approximately 2 hours, the tray is removed, and the product moved into an aeration chamber, in which clean, dry air is pumped through and out of the chamber, which effectively stops the crosslinking process. After a period of warming and vacuum, a highly porous, low density collagen matrix is formed within the 3D textile.

A 23 mm wide, 3 mm tall, and 30 mm long composite scaffold for Rotator Cuff repair or augmentation made from a three-dimensional PLLA textile filled with a highly porous collagen matrix is manufactured, as follows. A 5 mm wide, 3 mm tall, and 260 mm long composite scaffold for ACL repair or augmentation made from a three-dimensional PLLA textile filled with a highly porous collagen matrix is manufactured, as described hereafter. A three-dimensional (3D) textile which comprises the support structure is manufactured using the double pillar pattern illustrated in FIG. 2A in accordance with the technique the warp knitting technique described. The resulting structure has top and bottom layers of approximately 25 wales each. The corresponding wales top and bottom layers of the interconnected by a series of knitted spacing yarns extending through the void space in the Z direction and interconnecting the layers.

The 3D textile is received as a continuous length textile, 5 mm wide and 3 mm tall and is ultrasonically scoured, e.g. washed, in solution of DI and IPA to remove particulate and yarn spin finish. Multiple washes, replacing solution in between washes, are used. The temperature of the wash solution may be room temperature, or up to 40C. The 3D textile is then air dried, and cut to length. The scoured and cut to length of 3D textile is then submerged in a solution of PEG and ethanol to increase hydrophilicity. The concentration of PEG in ethanol is specifically controlled to result in a controlled weight percentage of PEG on the 3D textile. The 3D textile is then air dried.

Next, a 0.6% collagen solution by weight is made up using low molarity acetic acid and powder-form Type-1 bovine collagen is blended and vacuum processed to remove trapped air bubbles.

The stainless-steel mold shown in FIG. 5B is used to guide infill of collagen solution into the 3D textile and through the next step, Lyophilization, to create the collagen sponge matrix structure. The cavities of the mold are filled with a small amount of collagen solution. Then, 3D textile lengths are placed into the mold, 3D textile faces parallel to the bottom of the cavity, and clamps are used on each end to secure the 3D textiles and to prevent movement. These clamps have an additive benefit, in the following step, Lyophilization, by creating areas on each end that are flat without porous collagen matrix, used for product handling and suture attachment.

Then, additional collagen solution is filled into the cavities with the textile, completely submerging the textile in collagen solution. Then, the mold with textile and collagen solution is vacuum processed to remove remaining air within the 3D textile to completely infill the textile with solution. The mold, with textile and collagen solution, are placed into a shelf lyophilizer, and the temperature brought down to −55 C over a period of 2 hrs. A vacuum is pulled in the lyophilizer chamber, and the shelf temperature gradually increased, providing energy to the frozen solvent, allowing the process of sublimation to occur. The sublimated solvent is collected in a separate condenser and fully removed from the inflammation. After a period of warming and vacuum, a highly porous, low density collagen matrix is formed within the 3D textile.

The mold design may be such that the whole scaffold becomes encapsulated in the collagen gel this may have the benefit of shielding the body from the textile scaffold component with the more biocompatible collagen gel.

Medical Procedures

The composite scaffolds described herein may be utilized in a wide array of medical procedures including to reinforce a suture repair, stand alone repair or reconstruction, or reconstruction using a tissue graft and for fixation purposes. Reinforcement of a repair or reconstruction using the composite scaffold may be applicable to the knee, ankle, shoulder elbow and hand, and non-musculoskeletal soft tissue. The knee may include any of ACL (anterior cruciate ligament), PCL (posterior cruciate ligament), LCL (lateral collateral ligament), MCL (medical collateral ligament), MPFL (medial patellofemoral ligament), ALL (anterolateral ligament), and Posterolateral Corner Injury (fibular collateral ligament, popliteus tendon, popliteofibular ligament). The ankle may include any of the ATFL (anterior talofibular ligament) and CFL (calcaneofibular ligament). The shoulder elbow and hand, may include any of the rotor cuff (supraspinatus, infraspinatus, subscapularis, and teres minor tendons), acromioclavicular ligament, UCL (ulnar collateral ligament), and flexor tendon. Non-musculoskeletal soft tissue may include any of the breast, abdominal wall, and pelvic floor. The composite scaffolds described herein may be utilized for fixation of permanent and re-absorbable materials, including sutures, suture anchors, tacks, and staples.

The physical dimensions and biomechanical characteristics of the composite scaffolds disclosed herein are optimized for use in a wide array of medical procedures including to reinforce a suture repair, standalone repair or reconstruction, or reconstruction using a tissue graft and for fixation purposes. Reinforcement of a repair or reconstruction using the composite scaffold may be applicable to the knee, ankle, shoulder elbow and hand, and non-musculoskeletal soft tissue. Such physical characteristics are measurably different than those of commercially available products such as hernia mesh and orthopedic suture tape and are more suitable for the above described procedures. For example, orthopedic suture tape exists, and is measurable as a three-dimensional entity, for all intents and purposes relative to surgery it is effectively two-dimensional with little value for regenerating the volume of tissue necessary to enhance or mimic the characteristics of tendons or ligaments. For surgical meshes and patches constructed of bioresorbable materials, which have broad applications and can be considered scaffolds, the resulting tissue plane that is formed following total resorption of the material can be quite thin and weak; this is due to a lack of thickness and/or sufficient void volume of suitable pore size for cellular ingrowth within the scaffold. Therefore, there is a clear need to create tissue scaffolds of sufficient thickness that regenerate thicker and stronger tissue planes following polymeric degradation.

In an exemplary embodiment, FIG. 12 and Table 4 below illustrates, over the number of samples, that a tendon augmented by the disclosed composite scaffold, is consistently stronger and capable of handling greater force over similar extension than the tendon alone.

TABLE 4

|  | Sample 1 | Sample 2 | Sample 3 | Sample 4 |
| --- | --- | --- | --- | --- |
| Augmented (N) | 118.5 | 128 | 241 | 182.5 |
| Tendon Alone (N) | 81.5 | 97.5 | 202 | 150 |
| % Increase | 31% | 24% | 16% | 18% |

Another alternative form of the disclosed composite scaffold is utilizing a tubular spacer, whether warp or weft knit, which can be used as a "sheath" over autograft, allograft, or a repaired tendon or ligament. One method of producing this is to take a flat spacer fabric and then attach the opposing edges, by sewing, heat sealing, or other means, to create a tube, as illustrated in FIG. 14. Alternatively, a customized circular knitter can be used to knit a tubular spacer fabric without a connecting seam. Another alternative method of making a tubular spacer is to weave the structure by method of 3D circular woven preform, method and structure is illustrated in FIG. 15.

An alternative method of manufacturing the textile component, as the structure to hold the porous matrix, is to 3D print a structure from an elastic or non-elastic material, which will then be infilled with the porous matrix.

Alternatively, both the structure and the matrix can be 3D printed from one or multiple materials, either as separate but combined entities, or as a single entity that provides both strength, porosity, and resistance to compression.

In embodiments, the scaffold comprises a composite structure with a textile outer cover to provide strength and a 3D printed inner support structure to provide resistance to compression. Such scaffold may be either rectangular or tubular is shape. Braiding may be used as a cost effective method of producing a tubular structure. By braiding over a 3D printed inner support structure insert the required contiguous space for tissue ingrowth is provided. Polymer fibers braided longitudinally into an exterior braid structure may be provided to further modulate the tensile characteristics of the scaffold.

EXAMPLES

Example 1—Manufacture of Textile Scaffold

A 75 denier 30 filament poly-L-Lactic Acid (PLLA) yarn was produced for use in manufacture of scaffold fabrics. A warp beam was produced for use in a Karl Mayer Double Needle Bar Machine to produce the fabric. A 5 mm wide fabric of 6 wales across its width and a 23 mm wide fabric with 27 wales across were produced, i.e. using a 22 gauge needle bed. The two surface layers were separated in the Z direction by spacer yarns to make fabrics 2 mm thick. The fabric was scoured in an ultrasonic bath with a mixture of deionized water and iso propyl alcohol and dried.

Example 2—Manufacture of ACL Augmentation/Repair Device

A 0.6% collagen solution (by weight) was made up using low molarity Acetic Acid and powder-form Type-1 bovine collagen. This solution was blended and vacuum processed to remove trapped air bubbles. A stainless-steel mold, as shown in FIG. 5A, its cavities filled with a small amount of collagen solution. The textile scaffold from Example 1, a 26 cm long and 5 mm wide sample, were placed into the mold, with textile faces parallel to the bottom of the cavity, and clamps used on each end to secure the textile and prevent movement. Additional collagen solution was filled into the cavities with the textile, completely submerging the textile in collagen solution. The mold with textile and collagen solution was vacuum processed to remove remaining air within the textile to completely infill textile with solution.

The mold was then placed in an SP Scientific AdVantage Plus Lyophilizer and the samples lyophilized, the lyophilization process taking the interior of the Lyophilizer from room temperature to −55 C over a period of 2 hrs. The textile, infilled with a dry, highly porous and low-density collagen matrix, was removed from the mold cavities and placed into a sealed chamber on a wire rack. A formaldehyde and ethanol solution was poured into a tray, and the tray placed under the rack of product, and the chamber door sealed. Vapor from the solution crosslinks the collagen within the textile. After 2 hours, the tray was removed, and the product moved into an aeration chamber, in which clean, dry air was pumped through and out of the chamber, which effectively stops the crosslinking process. The final device was suitable for use in ACL augmentation or repair Example 3—Manufacture of Rotator Cuff Augmentation/Repair Device Following the methodology of Example 2 a mold suitable to accommodate a 23 mm wide fabric was used to impregnate 50 mm by 23 mm pieces of fabric from Example 1, but instead using the mold of FIG. 5B. The final device was suitable for use in rotator cuff augmentation or repair Example 4—Manufacture of Matrix Material A 0.6% collagen solution (by weight) was made up using low molarity Acetic Acid and powder-form Type-1 bovine collagen. This solution was blended and vacuum processed to remove trapped air bubbles. The solution was then lyophilized same as in Examples 2 and 3.

Example 5—Demonstration of Tendon Augmentation

A Porcine profundus tendon was obtained from a local abbatoir. The composite scaffold device from Example 1 was doubled over the tissue and whip-stitched at one end with #2 suture. A tensile test machine was used to mimic the graft preparation table. The whip-stitched end secured in upper grip jaws of tensile tester. Pretension achieved by loading both ends of composite scaffold to appropriate force and securing lower grip jaws. The construct was cycled to 3.75 mm extension and back to zero. The performance data are shown in Table 3 below, and demonstrated the ability of the composite scaffold pre tension to control the reinforcement provided by the scaffold.

TABLE 4

|  | Force at 3.75 mm (N) | Stiffness at 1 mm Displacement (N/mm) | Stiffness at 2 mm Displacement (N/mm) | Stiffness at 3 mm Displacement (N/mm) | Stiffness at 3.75 mm Displacement (N/mm) |
|---|---|---|---|---|---|
| Tendon Alone | 222 | 30 | 75 | 108.3 | 116.6 |
| Tendon with BioBrace Tensioned to 14N | 342 | 45.8 | 81.5 | 150 | 175 |
| Tendon with BioBrace Tensioned to 20N | 450 | 77.8 | 125 | 175 | 175 |

While the size of the composite scaffolds described herein may vary according to the intended application, it is contemplated that a scaffold may have a lengths up to 1000 mm and a width from 3 mm to 1000 mm to adopt to different soft-tissue sizes and applications. Further, the width may taper to suture width at the ends of the scaffold.

The present disclosure will be more completely understood through the following description, which should be read in conjunction with the drawings. In this description, like numbers refer to similar elements within various embodiments of the present disclosure. The skilled artisan will readily appreciate that the methods, apparatus and systems described herein are merely exemplary and that variations can be made without departing from the spirit and scope of the disclosure. The terms comprise, include, and/or plural forms of each are open ended and include the listed parts and can include additional parts that are not listed. The term and/or is open ended and includes one or more of the listed parts and combinations of the listed parts.

At various places in the present specification, values are disclosed in groups or in ranges. It is specifically intended that the description include each and every individual subcombination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Real numbers are intended to be similarly inclusive, including values up to at least three decimal places.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments.

As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents falling within the scope of the disclosure may be resorted to.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Moreover, while illustrative embodiments have been described herein, the scope of any and all embodiments include equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:
1. A composite scaffold comprising:
   a microporous matrix having a multitude of interconnected pores opening to an exterior surface of the microporous matrix and collectively defining an interior void space; and a structure supporting the microporous matrix comprising first and second outer layers separated by the interior void space, and a plurality of spacer elements yarns extending through the interior void space and connecting the first and second outer layers;

the composite scaffold having a substantially rectangular cross-section defined by exterior sides, and wherein a plurality of the interconnected pores proximate one of the exterior sides have a largest dimension oriented relative to the one exterior side.

2. The composite scaffold of claim 1 wherein at least approximately 60% of the void space comprises pores having a size dimension of at least 10 μm or greater.

3. The composite scaffold of claim 1 wherein a volume of the void space is between approximately 3.0 cm$^3$/gram and 9.0 cm$^3$/gram.

4. The composite scaffold of claim 1 wherein the composite scaffold has a cross sectional area of approximately between 3 mm$^2$ and 250 mm$^2$, and
wherein the cross-sectional area changes less than approximately 17% at a strain percentage of 13%.

5. The composite scaffold of claim 1 wherein a surface area of the composite scaffold is between approximately 0.3 m$^2$/gram and 1.5 m$^2$/gram.

6. The composite scaffold of claim 1 wherein the plurality of the interconnected pores have a largest dimension oriented between approximately between 45° and 135° relative to the one exterior side.

7. The composite scaffold of claim 1 wherein the plurality of the interconnected pores have a largest dimension oriented between approximately between 60° and 120° relative to the one exterior side.

8. The composite scaffold of claim 1 wherein the plurality of the interconnected pores have a largest dimension oriented between approximately between 75° and 105° relative to the one exterior side.

9. The composite scaffold of claim 1 wherein the composite scaffold has an ultimate stress of approximately between 2.5 MPa and 30 MPa.

10. The composite scaffold of claim 1 wherein the composite scaffold has a yield stress of approximately between 2.5 MPa and 30 MPa.

11. The composite scaffold of claim 1 wherein the composite scaffold has a modulus of approximately between 2.5 MPa and 70 MPa, wherein modulus is calculated using a cross-sectional area of material comprising the composite scaffold and the void space.

12. The composite scaffold of claim 1 wherein the composite scaffold has a modulus of approximately between 150 MPa and 600 MPa, wherein modulus is calculated using a cross-sectional area of only material comprising the composite scaffold.

13. The composite scaffold of claim 1 wherein the structure supporting the microporous matrix comprises a three-dimensional textile structure.

14. The composite scaffold of claim 1 wherein the microporous matrix comprises any of a sponge, foam, or textured fibers or yarns, or any combination thereof.

15. The composite scaffold of claim 1 wherein the microporous matrix comprises any of a freeze-dried sponge, open cell extrusion foam, particulate leached sponge, or any combination thereof.

16. The composite scaffold of claim 1 wherein the microporous matrix comprises any of a sponge, foam, or textured fibers or yarns, or any combination thereof disposed within the scaffold by any of knitting, weaving, lyophilization, particulate leaching, open cell extrusion, solvent casting, solid-state foaming, and cross-linking.

17. The composite scaffold of claim 1 wherein the microporous matrix comprises one of collagen and hydrogel.

18. The composite scaffold of claim 1 wherein the scaffold comprises monofilament, multifilament, or textured yarns, or any combination thereof, knitted into a three-dimensional structure.

19. The composite scaffold of claim 1 wherein the scaffold comprises any combination of synthetic bioresorbable polymers, natural polymers and/or additives.

20. The composite scaffold of claim 1 wherein the scaffold comprises any of homopolymers, copolymers, or polymer blends of any of the following:
polylactic acid, polyglycolic acid, polycaprolactone, polydioxanone, polyhydroxyalkanoates, polyanhydrides, poly(ortho esters), polyphosphazenes, poly (amino acids), polyalkylcyanoacrylates, poly(propylene fumarate, trimethylene carbonate, poly(glycerol sebacate), poly(glyconate), poly(ethylene glycol), poly (vinyl alcohol) and polyurethane, or any combination thereof.

21. The composite scaffold of claim 1 wherein at least approximately 70% of the void space comprises pores having a size dimension of 10 μm or greater.

22. The composite scaffold of claim 1 wherein at least approximately 80% of the void space comprises pores having a size dimension of 10 μm or greater.

23. The composite scaffold of claim 1 wherein the composite scaffold has a stiffness of approximately between 2.5 N/mm and 25 N/mm.

24. The composite scaffold of claim 1 wherein the composite scaffold has an ultimate load of approximately between 20% and 70%.

25. The composite scaffold of claim 1 wherein the composite scaffold has an ultimate load approximately between 100 N and 200 N.

26. The composite scaffold of claim 1 wherein a surface area of the composite scaffold is between approximately 0.3 m$^2$/gram and 15.0 m$^2$/gram.

27. The composite scaffold of claim 1 wherein a surface area of the composite scaffold is between approximately 0.6 m$^2$/gram and 1.2 m$^2$/gram.

28. The composite scaffold of claim 1 wherein a surface area of the composite scaffold is between approximately 0.7 m$^2$/gram and 1.0 m$^2$/gram.

29. The composite scaffold of claim 1 wherein the microporous matrix comprises a multitude of interconnected pores having a median pore size of between approximately 10 μm to 100 μm.

30. The composite scaffold of claim 1 wherein the microporous matrix comprises a multitude of interconnected pores having a median pore size of between approximately 12 μm to 70 μm.

31. The composite scaffold of claim 1 wherein the microporous matrix comprises a multitude of interconnected pores having a median pore size of between approximately 20 μm to 40 μm.

* * * * *